US008906853B2

(12) United States Patent
Or et al.

(10) Patent No.: US 8,906,853 B2
(45) Date of Patent: Dec. 9, 2014

(54) [N-ME-4-HYDROXYLEUCINE]-9-CYCLOSPORIN ANALOGUES FOR TREATMENT AND PREVENTION OF HEPATITIS C INFECTION

(71) Applicant: Enanta Pharmaceuticals, Inc., Watertown, MA (US)

(72) Inventors: Yat Sun Or, Watertown, MA (US); In Jong Kim, Lexington, MA (US); Jiang Long, Wayland, MA (US); Lijuan Jiang, Newton, MA (US); Sheng Sean Liu, Shrewsbury, MA (US); Guoqiang Wang, Belmont, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 14/092,171

(22) Filed: Nov. 27, 2013

(65) Prior Publication Data

US 2014/0154208 A1 Jun. 5, 2014

Related U.S. Application Data

(60) Provisional application No. 61/730,828, filed on Nov. 28, 2012.

(51) Int. Cl.
| A61K 38/21 | (2006.01) |
| A61K 31/7056 | (2006.01) |
| A61K 45/06 | (2006.01) |
| C07K 7/64 | (2006.01) |
| A61K 31/713 | (2006.01) |

(52) U.S. Cl.
CPC ............. *C07K 7/645* (2013.01); *A61K 31/7056* (2013.01); *A61K 38/21* (2013.01); *A61K 45/06* (2013.01); *A61K 31/713* (2013.01)
USPC ............... 514/9.1; 514/10; 530/317

(58) Field of Classification Search
None
See application file for complete search history.

(56) References Cited

U.S. PATENT DOCUMENTS

| 4,108,985 | A | 8/1978 | Ruegger et al. |
| 4,220,641 | A | 9/1980 | Traber et al. |
| 4,288,431 | A | 9/1981 | Traber et al. |
| 4,384,996 | A | 5/1983 | Bollinger et al. |
| 4,396,542 | A | 8/1983 | Wenger |
| 4,554,351 | A | 11/1985 | Wenger |
| 4,771,122 | A | 9/1988 | Seebach |
| 4,798,823 | A | 1/1989 | Witzel |
| 5,239,057 | A | 8/1993 | Wang et al. |
| 5,284,826 | A | 2/1994 | Eberle |
| 5,525,590 | A | 6/1996 | Bollinger et al. |
| 5,604,092 | A | 2/1997 | Erlanger et al. |
| 6,784,156 | B2 | 8/2004 | Or et al. |
| 6,809,077 | B2 | 10/2004 | Or et al. |
| 6,927,208 | B1 | 8/2005 | Wenger et al. |
| 6,979,671 | B2 | 12/2005 | Or et al. |
| 7,012,064 | B2 | 3/2006 | Or et al. |
| 7,012,065 | B2 | 3/2006 | Or et al. |
| 7,438,920 | B1 | 10/2008 | Kim et al. |
| 7,468,419 | B2 | 12/2008 | Wu et al. |
| 8,178,531 | B2 | 5/2012 | Or et al. |
| 8,349,312 | B2 * | 1/2013 | Wang et al. .................. 424/85.4 |
| 8,367,053 | B2 * | 2/2013 | Long et al. .................. 424/85.4 |
| 8,367,617 | B2 | 2/2013 | Phiasivongsa et al. |
| 8,481,483 | B2 | 7/2013 | Or et al. |
| 8,623,814 | B2 * | 1/2014 | Or et al. ......................... 514/3.7 |
| 8,685,917 | B2 * | 4/2014 | Gao et al. ........................ 514/2.9 |
| 2002/0142946 | A1 | 10/2002 | Or et al. |
| 2003/0087813 | A1 | 5/2003 | Or et al. |
| 2003/0104992 | A1 | 6/2003 | Or et al. |
| 2006/0069015 | A1 * | 3/2006 | Molino et al. .................... 514/9 |
| 2007/0213301 | A1 | 9/2007 | Zhang et al. |
| 2007/0249527 | A1 * | 10/2007 | Wu et al. ........................... 514/9 |
| 2008/0214447 | A1 | 9/2008 | Kobayashi et al. |
| 2010/0196316 | A1 | 8/2010 | Or et al. |
| 2010/0209390 | A1 | 8/2010 | Or et al. |
| 2011/0008284 | A1 | 1/2011 | Gao et al. |
| 2011/0008285 | A1 | 1/2011 | Long et al. |
| 2011/0008286 | A1 | 1/2011 | Wang et al. |
| 2011/0206637 | A1 | 8/2011 | Or et al. |
| 2011/0218175 | A1 | 9/2011 | Or et al. |
| 2013/0183267 | A1 | 7/2013 | Or et al. |

FOREIGN PATENT DOCUMENTS

| EP | 0034567 A2 | 8/1981 |
| EP | 0056782 A1 | 7/1982 |
| EP | 0300784 A2 | 1/1989 |
| EP | 0300785 A2 | 1/1989 |
| GB | 2206119 A | 12/1988 |

(Continued)

OTHER PUBLICATIONS

Wilson, et al., "RNA interference blocks gene expression and RNA synthesis from hepatitis C replicons propagated in human liver cells," PNAS, 100(5):2783-2788, 2003.
Nakagawa, et al., "Suppression of Hepatitis C Virus Replication by Cyclosporin A is Mediated by Blockade of Cyclophilins", Gastroenterology, Elsevier, Philadelphia, PA, 129(3):1031-1041, 2005.
Freidinger, R.M., et al., "Synthesis of 9-Fluorenylmethyloxycarbonyl-Protected N-Alkyl Amino Acids by Reduction of Oxazoiidinones", J. Org. Chem., 48:77-81, 1983.
International Search Report for PCT/US2010/22675, dated Mar. 23, 2010.
Kobel, et al., "Directed Biosynthesis of Cyclosporins," Europ. J. Applied Microbiology and Biotechnology, 14:273-240 1982.

(Continued)

*Primary Examiner* — Karlheinz R Skowronek
*Assistant Examiner* — Mindy Newman
(74) *Attorney, Agent, or Firm* — Edgar W. Harlan; Carolyn S. Elmore, Esq.; Elmore Patent Law Group, P.C.

(57) ABSTRACT

The present invention relates to novel cyclosporine analogues having antiviral activity against HCV and useful in the treatment of HCV infections. More particularly, the invention relates to novel cyclosporine analogue compounds, compositions containing such compounds and methods for using the same, as well as processes for making such compounds.

12 Claims, No Drawings

(56) References Cited

FOREIGN PATENT DOCUMENTS

| | | |
|---|---|---|
| GB | 2207678 A | 2/1989 |
| WO | 8602080 A1 | 4/1986 |
| WO | 9918120 A1 | 4/1999 |
| WO | 03033526 A2 | 4/2003 |
| WO | 2005021028 A1 | 3/2005 |
| WO | 2006005610 A1 | 1/2006 |
| WO | 2006038088 A1 | 4/2006 |
| WO | 2006039668 A2 | 4/2006 |
| WO | 2007041631 A1 | 4/2007 |
| WO | 2007049803 A1 | 5/2007 |
| WO | 2007112345 A2 | 10/2007 |
| WO | 2007112352 A2 | 10/2007 |
| WO | 2007112357 A2 | 10/2007 |
| WO | 2008139986 A1 | 11/2008 |
| WO | 2012009715 A2 | 1/2012 |
| WO | 2012021796 A2 | 2/2012 |

OTHER PUBLICATIONS

Von Wartburg, et al., "Chemistry of the Natural Cyclosporin Metabolites", Progress in Allergy, 38:28-45, 1986.

Wenger, R., "Synthesis of Cyclosporine and Analogues: Structures, Activity, Relationships of New Cycloporine Derivatives", Transpl. Proc., XV(4):Suppl. 1, pp. 2230-2241, 1983.

Wenger, "Cyclosporine and Analogues—Isolation and Synthesis—Mechanism of Action and Structural Requirements for Pharmacological Activity," Progress in the Chemistry of Organic Natural Products, 50:123-168, 1986.

Watashi et al., "Cyclosporin A Suppresses Replication of Hepatitis C Virus Genome in Cultured Hepatocytes," Hepatology, 38(5):1282-1288, 2003.

Nakagawa et al., "Specific Inhibition of Hepatitis C Virus Replication by Cyclosporin A", Biochem. Biophys. Res. Commun., 313:42-47, 2004.

Shimotohno, et al., "Inhibitory Role of Cyclosporin A and its Derivatives on Replication of Hepatitis C Virus", American Transplant Congress, Abstract No. 648 (American Journal of Transplantation, 4(s8):334-335, 2004.

Inoue, et al., "Combined Interferon α2b and Cyclosporin A in the Treatment of Chronic Hepatitis C: Controlled Trial", Journal of Gastroenterology, 38:567-572, 2003.

Papageorgiou, C., et al., "Improved Binding Affinity for Cyclophilin A by a Cyclosporin Derivative Singly Modified at Its Effector Domain", J. Med. Chem. 37:3674-3676, 1994.

Paeshuyse, et al., "Potent and Selective Inhibition of Hepatitis C Virus Replication by the Non-Immunosuppressive Cyclosporin Analogue DEBIO-025," Antiviral Research 65(3):A41, 2005.

Flisiak, R., et al., "The Cyclophilin Inhibitor Debio-025 Shows Potent Anti-Hepatitis C Effect in Patients Coinfected with Hepatitis C and Human Immunodeficiency Virus", Hepatology, 47(3);817-826, 2008.

Ma, S., et al., "NIM811, a Cyclophilin Inhibitor, Exhibits Potent In Vitro Activity against Hepatitis C Virus Alone or in Combination with Alpha Interferon", Antimicrobial Agents and Chemotherapy, 50(9):2976-2982, Sep. 2006.

Robida, J.M., et al., "Characterization of Hepatitis C Virus Subgenomic Replicon Resistance to Cyclosporine in Vitro", Journal of Virology, 81(11):5829-5840, 2007.

Flisiak, R., et al., "Cyclophilin Inhibitors in Hepatitis C Viral Infection", Expert Opin. Investig. Drugs, 16(9):1345-1354, 2007.

Papageorgiou, C., et al., "Calcineurin Has a Very Tight-Binding Pocket for the Side Chain of Residue 4 of Cyciosporin", Bioorganic & Medicinal Chemistry Letters, 4(2):267-272, 1994.

* cited by examiner

US 8,906,853 B2

[N-ME-4-HYDROXYLEUCINE]-9-CYCLOSPORIN ANALOGUES FOR TREATMENT AND PREVENTION OF HEPATITIS C INFECTION

RELATED APPLICATION

This application claims the benefit of U.S. Provisional Application No. 61/730,828, filed on Nov. 28, 2012. The entire teachings of the above application are incorporated herein by reference.

TECHNICAL FIELD

The present invention relates to novel cyclosporine analogues having antiviral activity against HCV and useful in the treatment of HCV infections. More particularly, the invention relates to novel cyclosporine analogue compounds, compositions containing such compounds and methods for using the same, as well as processes for making such compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Due to the high degree of variability in the viral surface antigens, existence of multiple viral genotypes, and demonstrated specificity of immunity, the development of a successful vaccine in the near future is unlikely. Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

Cyclosporin A (CsA), a neutral cyclic undecapeptide isolated from the fungus *Tolypocladium injlaturn* and currently marketed as NEORAL® and SANDIMMUNE® (Novartis, Basel, Switzerland), has been widely used for the prevention of organ transplant rejection. The molecular basis for the immunosuppressant activity of cyclosporin A and cyclosporin analogues begins with the passive diffusion of the cyclosporin (Cs) molecule into the cell, followed by binding to its intracellular receptor, cyclophilin A (CypA). CypA belongs to a family of proteins that catalyze cis-trans peptidyl-prolyl isomerization, i.e., PPIase, a rate-limiting step in protein folding. CsA and other cyclosporin analogues bind to the active site of CypA. However, immunosuppression is not believed to be due to the inhibition of CypA PPIase activity. The target of the CsA-CypA complex is a $Ca^{2+}$-calmodulin-dependent serine-threonine-specific protein phosphatase, calcineurin. In T-cells responding to antigen presentation, an increase in intracellular $Ca^{2+}$ activates calcineurin, which subsequently dephosphorylates the transcription factor called the nuclear factor of activated T-cells ("NFAT"). Dephosphorylated NFAT undergoes a molecular change, e.g., homodimerization that allows it to cross into the nucleus, and promotes the expression of T-cell activation genes. CsA and other immunosuppressive cyclosporin derivatives inhibit calcineurin which results in the inhibition of expression of cytokine genes, e.g., interleukin-2 (IL-2) that promotes T-cell activation and proliferation, i.e., immunosuppressive activity.

Cyclosporine A and certain derivatives have been reported as having anti-HCV activity, see Watashi et al., *Hepatology*, 2003, Volume 38, pp 1282-1288, Nakagawa et al., *Biochem. Biophys. Res. Commun.* 2004, Volume 313, pp. 42-7, and Shimotohno and K. Watashi, 2004 American Transplant Congress, Abstract No. 648 (*American Journal of Transplantation* 2004, Volume 4, Issue s8, Pages 1-653). The authors of the Nakagawa et al. paper state that certain chaperone activities, such as those of cyclophilins, may be crucial for the processing and maturation of the viralproteins and for viral replication. Cyclosporine derivatives having HCV activity are known from International Publication No's. WO 2005/021028, WO 2006/039668, WO 2006/038088, WO 2006/039688, WO 2007/112352, WO 2007/112357, WO 2007/112345, WO 2007/041631, WO 2008/139986 and WO 2012/009715.

A subsequent controlled clinical trial showed that a combination of cyclosporin A with interferon α2b is more effective than interferon monotherapy, especially in patients with high viral loads (Inoue et al., "Combined Interferon α2b nd Cyclosporin A in the Treatment of Chronic Hepatitis C: Controlled Trial," *J. Gastroenterol.* 38:567-572 (2003)).

PCT International Patent Publication No. WO 2006/005610 recently described the use of a combination of cyclosporin A and pegylated interferon for treating hepatitis C viral infection. In addition, PCT International Patent Publication No. WO 2005/021028 relates to the use of non-immunosuppressive cyclosporine for treatment of HCV disorders. Also, Paeshuyse et al., "Potent and Selective Inhibition of Hepatitis C Virus Replication by the Non-Immunosuppressive Cyclosporin Analogue DEBIO-025," *Antiviral Research* 65(3):A41 (2005) recently published results for a non-immunosuppressive cyclosporin analogue, DEBIO-025, that exhibited potent and selective inhibition of hepatitis C virus replication. Debio-025 does possess potent binding affinity for cyclophilin A.

SUMMARY OF THE INVENTION

The present invention relates to novel Cyclosporin analogues represented herein below, pharmaceutical compositions comprising such compounds, and methods for the treatment of viral (particularly hepatitis C viral) infection in a subject in need of such therapy with said compounds.

In its principal embodiment, the present invention provides a compound of formula (I) or (II);

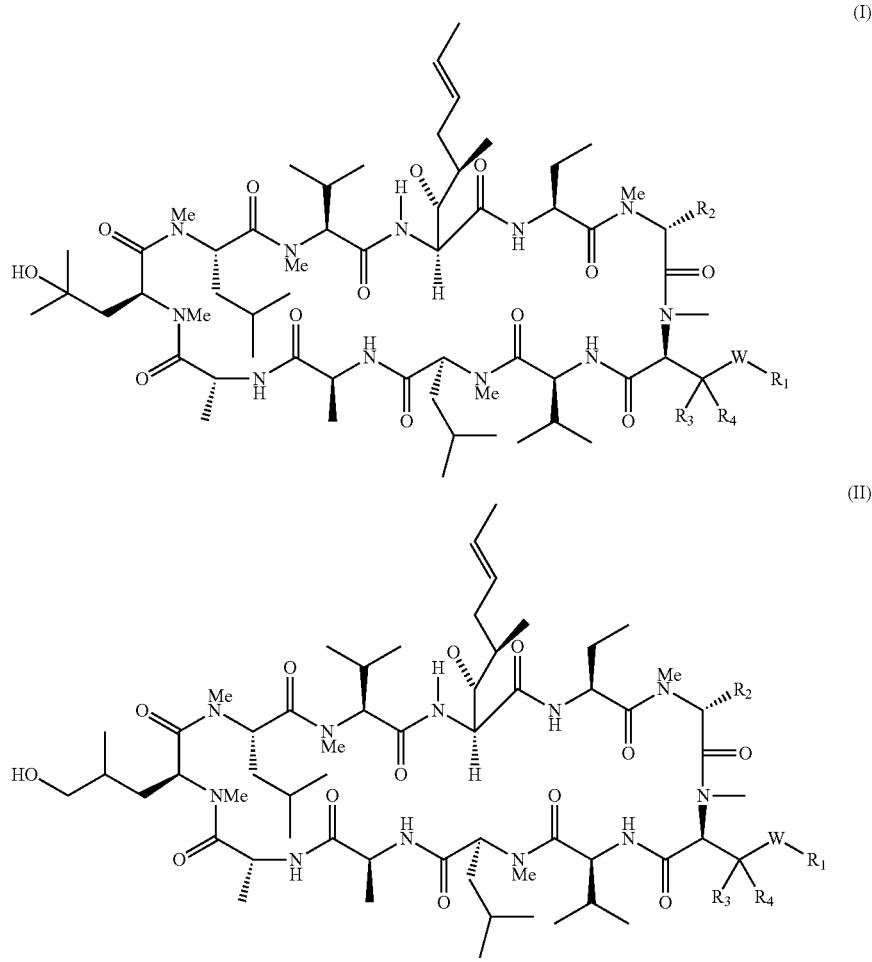

Wherein:
R₁ is selected from:
a) $R_{11}$, where $R_{11}$ is selected from:
1) Hydrogen;
2) Deuterium;
3) $C_1$-$C_8$ alkyl;
4) Substituted $C_1$-$C_8$ alkyl;
5) $C_2$-$C_8$ alkenyl;
6) Substituted $C_2$-$C_8$ alkenyl;
7) $C_2$-$C_8$ alkynyl;
8) Substituted $C_2$-$C_8$ alkynyl;
9) $C_3$-$C_{12}$ cycloalkyl;
10) Substituted $C_3$-$C_{12}$ cycloalkyl;
11) Aryl;
12) Substituted aryl;
13) Heterocycloalkyl;
14) Substituted heterocycloalkyl;
15) Heteroaryl; or
16) Substituted heteroaryl;
b) —C(O)N($R_{12}$)($R_{13}$), wherein $R_{12}$ and $R_{13}$ are independently selected from $R_{11}$ and $R_{11}$ is as previously defined or $R_{12}$ and $R_{13}$ combined together with the N which attached to is substituted or unsubstituted heterocycloalkyl;
c) $R_{14}$, where $R_{14}$ is selected from:
1) -M-$R_{11}$, wherein $R_{11}$ is as previously defined and M is selected from:
i. $C_1$-$C_8$ alkylene;
ii. Substituted $C_1$-$C_8$ alkylene;
iii. $C_2$-$C_8$ alkenylene;
iv. Substituted $C_2$-$C_8$ alkenylene;
v. $C_2$-$C_8$ alkynylene;
vi. Substituted $C_2$-$C_8$ alkynylene;
vii. $C_3$-$C_{12}$ cycloalkylene;
viii. Substituted $C_3$-$C_{12}$ cycloalkylene;
2) -M-N$R_{15}R_{18}$, wherein $R_{15}$ and $R_{18}$ are independently selected from $R_{11}$, or $R_{15}$ and $R_{18}$ are taken together with the nitrogen atom to which they are attached to form a substituted or unsubstituted heterocycloalkyl, and M is as previously defined;
3) -M-S(O)$_m R_{11}$, wherein m=0, 1, or 2; M and $R_{11}$ are as previously defined;
4) -M-O$R_{11}$, wherein M and $R_{11}$ are as previously defined;
5) -M-C(O)$R_{16}$, wherein M is as previously defined and $R_{16}$ is selected from:
i. $C_1$-$C_8$ alkyl;
ii. Substituted $C_1$-$C_8$ alkyl;
iii. $C_2$-$C_8$ alkenyl;
iv. Substituted $C_2$-$C_8$ alkenyl;
v. $C_2$-$C_8$ alkynyl;
vi. Substituted $C_2$-$C_8$ alkynyl;
vii. $C_3$-$C_{12}$ cycloalkyl; and
viii. Substituted $C_3$-$C_{12}$ cycloalkyl;
6) -M-OC(O)$R_{16}$, wherein M and $R_{16}$ are as previously defined;
7) -M-OC(O)O$R_{16}$, wherein M and $R_{16}$ are as previously defined;

8) -M-NR$_{17}$C(O)R$_{16}$, wherein R$_{17}$ is R$_{11}$, and M and R$_{16}$ are as previously defined;
9) -MNR$_{17}$C(O)OR$_{16}$, wherein R$_{17}$, M and R$_{16}$ are as previously defined;
10) -M-C(O)NR$_{17}$R$_{11}$, wherein R$_{17}$, M and R$_{11}$ are as previously defined;
11) -M-C(O)N(R$_{17}$)—OR$_{11}$, wherein R$_{17}$, M and R$_{11}$ are as previously defined;
12) -M-OC(O)NR$_{17}$R$_{18}$, wherein R$_{17}$, M and R$_{18}$ are as previously defined;
13) -M-NR$_{17}$C(O)NR$_{16}$R$_{18}$, wherein M, R$_{16}$, R$_{17}$ and R$_{18}$ are as previously defined or R$_{16}$ and R$_{18}$ are taken together with the nitrogen atom to which they are attached to form a substituted or unsubstituted heterocycloalkyl;
14) -M-C(S)SR$_{11}$, wherein M and R$_{11}$ are as previously defined;
15) -M-OC(S)SR$_{16}$, wherein M and R$_{16}$ are as previously defined;
16) -M-NR$_{17}$C(O)SR$_{16}$, wherein M, R$_{17}$ and R$_{16}$ are as previously defined;
17) -M-SC(O)NR$_{17}$R$_{18}$, wherein M, R$_{17}$ and R$_{18}$ are as previously defined or R$_{17}$ and R$_{18}$ are taken together with the nitrogen atom to which they are attached to form a substituted or unsubstituted heterocycloalkyl;
18) -M-CH=N—OR$_{11}$, wherein M and R$_{11}$ are as previously defined;
19) -M-CH=N—NR$_{17}$R$_{18}$, wherein M, R$_{17}$ and R$_{18}$ are as previously defined or R$_{17}$ and R$_{18}$ are taken together with the nitrogen atom to which they are attached to form a substituted or unsubstituted heterocycloalkyl;

W is absent, or —O—, or —S(O)$_m$—, wherein m=0, or 1, or 2; preferably W is —O—; and R$_2$, R$_3$ and R$_4$ are independently selected from hydrogen or methyl; preferably, R$_2$ is methyl; preferably one of R$_3$ and R$_4$ is methyl and the other is hydrogen.

In another embodiment of the compounds of formulas I and II, R$_1$ is —C(O)R$_{11}$, where R$_{11}$ is as defined above. In this embodiment, R$_1$ is preferably —C(O)—C$_1$-C$_7$-alkyl, such as acetyl, propionyl, butyryl or isobutyryl. More preferably, R$_1$ is acetyl.

In preferred embodiments, the group

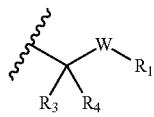

is represented by

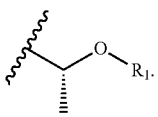

R$_1$ is preferably C$_1$-C$_8$ alkyl, substituted C$_1$-C$_8$ alkyl, C$_2$-C$_8$ alkenyl, substituted C$_2$-C$_8$ alkenyl or —C(O)—C$_1$-C$_6$-alkyl.

In certain embodiments, R$_1$ is acyl, such as C$_1$-C$_7$-alkanoyl; C$_1$-C$_5$-alkyl-Y or C$_2$-C$_5$-alkenyl-Y, where Y is H; optionally substituted aryl, preferably optionally substituted phenyl; optionally substituted heterocyclyl; —OC(O)R$_5$; NR$_5$R$_6$; OH; —O—(CH$_2$)$_n$—X, where n is 1 to 4 and X is heterocyclyl; —OC(O)NR$_5$R$_6$; —C(O)H; —CH=NOZ, where Z is H, alkyl, aryl, arylalkyl, heteroaryl or heteroarylalkyl, each optionally substituted; —CH(OR$_5$)$_2$; —SC(O)R$_5$; —SH; —OSO$_2$R$_5$; —C(O)OH; —C(O)N(R$_8$)OH, where R$_8$ is hydrogen or C$_1$-C$_4$-alkyl; N$_3$; —CN; or halogen, preferably fluorine. R$_5$ and R$_6$ are independently H; optionally substituted alkyl, optionally substituted alkenyl, optionally substituted aryl, optionally substituted heteroaryl, optionally substituted arylalkyl or optionally substituted heteroarylalkyl. Alternatively, R$_5$, R$_6$ and the nitrogen atom to which they are attached form an optionally substituted heterocyclic.

In particularly preferred embodiments, R$_1$ is acetyl; C$_1$-C$_4$-alkyl-Y or C$_2$-C$_4$-alkenyl-Y, where Y is H; OH; optionally substituted phenyl; optionally substituted —O-phenyl; optionally substituted —S-phenyl; optionally substituted 5-membered heteroaryl; optionally substituted —O-5-membered heteroaryl; optionally substituted —S-5-membered heteroaryl; —OC(O)NR$_5$R$_6$, —NHC(O)OR$_5$, C(O)OR$_7$, —OC(O)OR$_7$, —CN, —N$_3$, —C(O)NR$_5$R$_6$, —C(O)R$_5$, optionally substituted —OSO$_2$-phenyl, —NHC(O)R$_5$, —CH=NOZ, where Z is —CH$_2$-heteroaryl-heteroaryl; —CH=N—NR$_5$R$_6$; or —NR$_5$R$_6$. R$_7$ is optionally substituted alkyl, optionally substituted alkenyl, optionally substituted aryl, optionally substituted heteroaryl, optionally substituted arylalkyl or optionally substituted heteroarylalkyl. In this embodiment, 5-membered heteroaryl is preferably imidazolyl, triazolyl or tetrazolyl, optionally fused to a benzo ring or a 6-membered nitrogen-containing heteroaryl ring. In this embodiment, R$_1$ is preferably C$_3$-C$_4$-alkyl-Y or C$_3$-C$_4$-alkenyl-Y.

In certain embodiments, R$_1$ is selected from the groups set forth below.

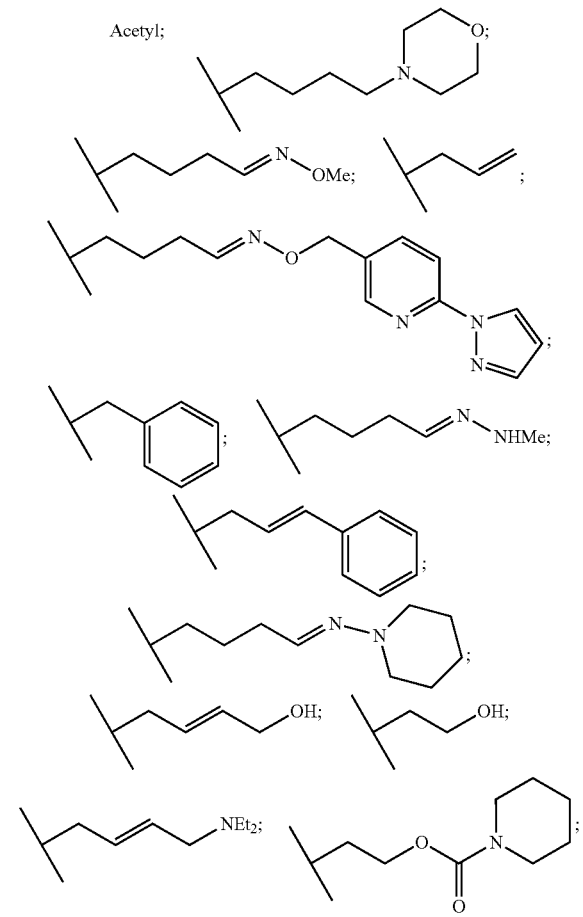

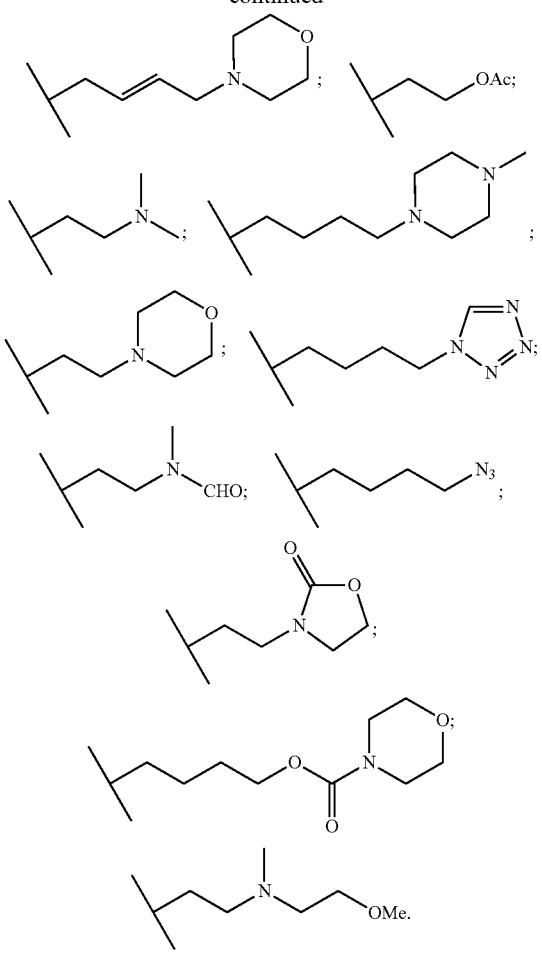

In preferred embodiments, R₁ is

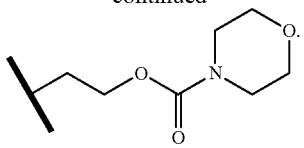

or

In another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In yet another embodiment, the present invention provides a method of inhibiting the replication of an RNA-containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of hepatitis C virus.

In still another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

In a first embodiment of the present invention is a compound of formula (I) as illustrated above, or a pharmaceutically acceptable salt, ester or prodrug thereof.

Representative subgenera of the present invention include a compound which is represented by the formula (III) or (IV):

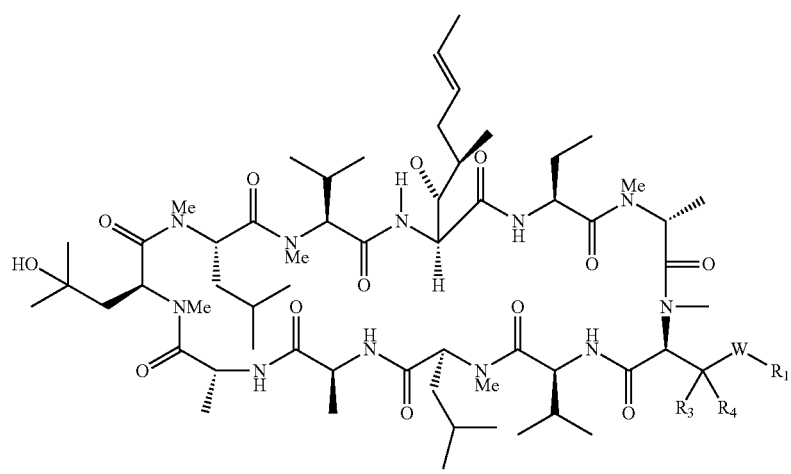

(III)

(IV)
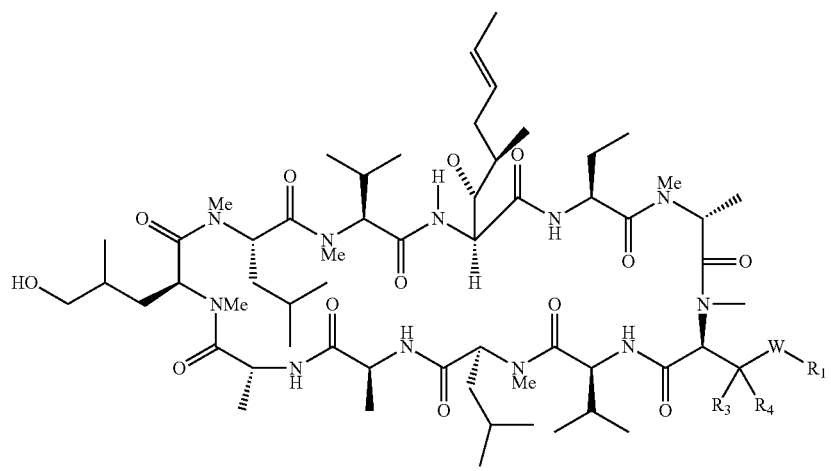
wherein, $R_1$, $R_3$, $R_4$, and W are defined previously;
a compound which is represented by the formula (V) or (VI):
(V)
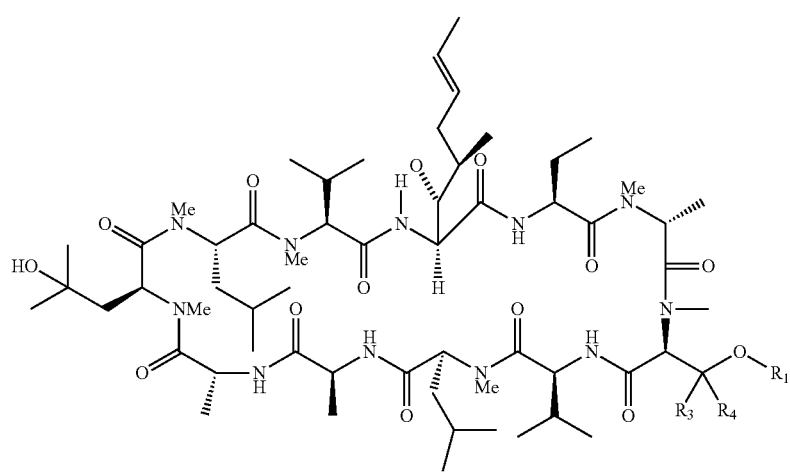
(VI)
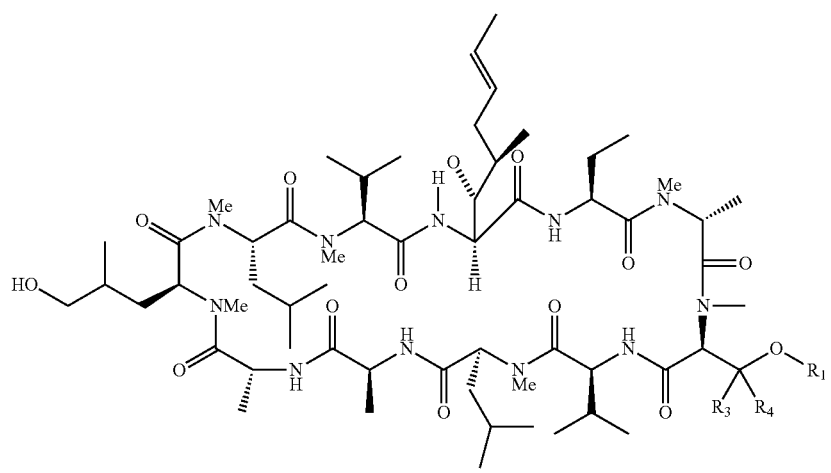
wherein, $R_1$, $R_3$, and $R_4$ are as defined previously; and a compound which is represented by formula (VII) or (VIII):

(VII)

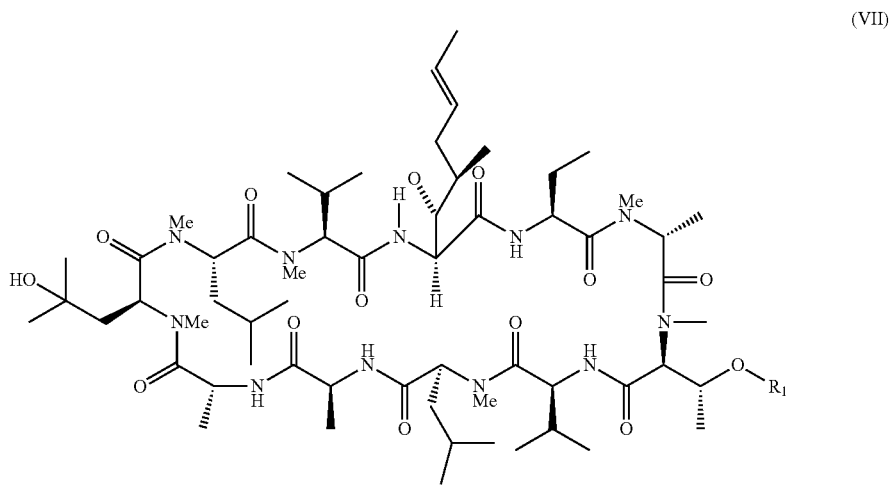

(VIII)

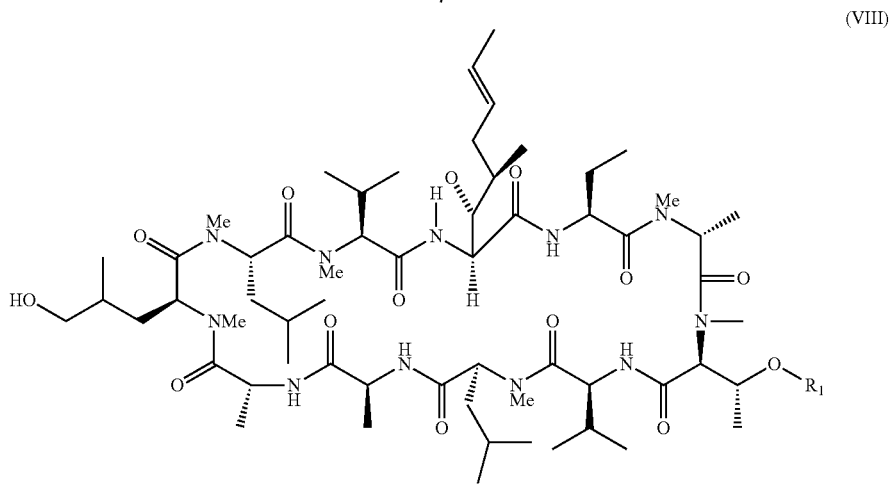

wherein $R_1$ is as defined previously.

Representative compounds of the invention include, but are not limited to, the compounds according to formula (VII) and formula (VIII), wherein for each formula $R_1$ is selected from the groups set forth in Table 1.

TABLE 1

| Example | $R_1$ |
|---|---|
| 1 | morpholine-butyl group |
| 2 | allyl group |
| 3 | benzyl group |

TABLE 1-continued

| Example | $R_1$ |
|---|---|
| 4 | cinnamyl group |
| 5 | 4-hydroxy-but-2-enyl group |
| 6 | 4-(diethylamino)-but-2-enyl group |
| 7 | 4-morpholinobut-2-enyl group |
| 8 | Ac |

TABLE 1-continued

| Example | R₁ |
|---|---|
| 9 | 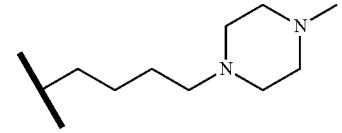 |
| 10 | 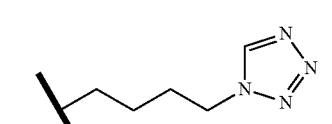 |
| 11 | 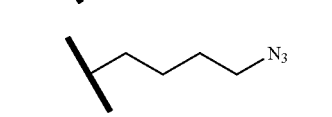 |
| 12 | 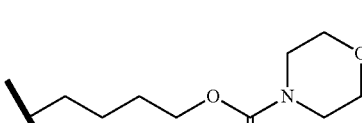 |
| 13 | 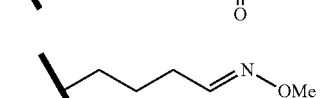 |
| 14 | 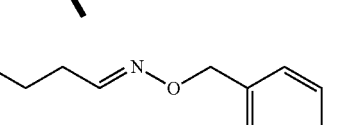 |
| 15 |  |
| 16 | 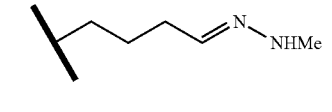 |
| 17 | 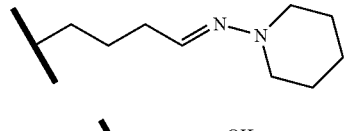 |
| 18 |  |
| 19 | 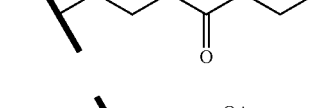 |
| 20 | 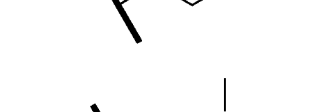 |
| 21 | 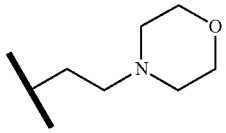 |
| 22 | 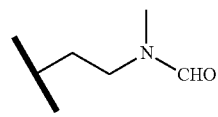 |
| 23 | 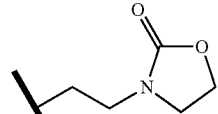 |
| 24 | 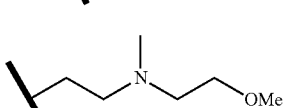 |

A further embodiment of the present invention includes pharmaceutical compositions comprising any single compound delineated herein, or a pharmaceutically acceptable salt, ester, solvate, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, solvate, or prodrug thereof, with a pharmaceutically acceptable carrier or excipient.

Yet a further embodiment of the present invention is a pharmaceutical composition comprising any single compound delineated herein in combination with one or more HCV compounds known in the art, or a pharmaceutically acceptable salt, ester, solvate, or prodrug thereof, with a pharmaceutically acceptable carrier or excipient.

It will be appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

It will be further appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It will be further appreciated that the compounds of the invention, or their pharmaceutically acceptable salts, stereoisomers, tautomers, prodrugs or salt of a prodrug thereof, can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01/90121(A2), or U.S. Pat. No. 6,348,587 B1 or WO 01/60315 or WO 01/32153 or non-nucleoside inhibitors such as, for example, benzimidazole polymerase inhibitors described in EP 1162196A1 or WO 02/04425.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenofovir, or any combination thereof. Examples of the RNA-containing virus include, but are not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined hereinabove, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms alkyl as used herein, refer to saturated, straight- or branched-chain hydrocarbon radicals. $C_1$-$C_8$ alkyl and $C_1$-$C_{12}$ alkyl, for example, refer to such radicals containing between one and eight, or one and twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "alkenyl," as used herein, refer to a straight- or branched-chain hydrocarbon radical having at least one carbon-carbon double bond by the removal of a single hydrogen atom. "$C_2$-$C_8$-alkenyl" for example, refers to such groups containing from two to eight carbon atoms. Alkenyl groups include, but are not limited to, for example, ethenyl, propenyl, butenyl, 1-methyl-2-buten-1-yl, heptenyl, octenyl, and the like.

The term "alkynyl", as used herein, refer to a straight- or branched-chain hydrocarbon radical containing having at least one carbon-carbon triple bond by the removal of a single hydrogen atom. "$C_2$-$C_8$ alkynyl", for example, refers to such groups containing from two to eight carbon atoms. Representative alkynyl groups include, but are not limited to, for example, ethynyl, 1-propynyl, 1-butynyl, heptynyl, octynyl, and the like.

The term "cycloalkyl" as used herein, refers to a monocyclic or polycyclic saturated carbocyclic ring compound. "$C_3$-$C_8$-cycloalkyl" and "$C_3$-$C_{12}$-cycloalkyl", for example, refer to such radicals containing from three to eight or from three to twelve carbon atoms respectively. Examples of $C_3$-$C_8$-cycloalkyl groups include, but are not limited to, cyclopropyl, cyclobutyl, cyclopentyl, cyclohexyl, cyclopentyl and cyclooctyl; examples of $C_3$-$C_{12}$-cycloalkyl groups include, but are not limited to, cyclopropyl, cyclobutyl, cyclopentyl, cyclohexyl, bicyclo [2.2.1] heptyl, and bicyclo [2.2.2] octyl.

The term "cycloalkenyl" as used herein, refers to a monocyclic or polycyclic carbocyclic radical having at least one carbon-carbon double bond. "$C_3$-$C_8$-cycloalkenyl" and "$C_3$-$C_{12}$-cycloalkenyl", for example, refer to such radicals containing from three to eight or from three to twelve carbon atoms respectively. Examples of $C_3$-$C_8$ cycloalkenyl groups include, but are not limited to, cyclopropenyl, cyclobutenyl, cyclopentenyl, cyclohexenyl, cycloheptenyl, cyclooctenyl, and the like; and examples of $C_3$-$C_{12}$ cycloalkenyl groups include, but are not limited to, cyclopropenyl, cyclobutenyl, cyclopentenyl, cyclohexenyl, cycloheptenyl, cyclooctenyl, and the like.

It is understood that any alkyl, alkenyl, alkynyl, cycloalkyl and cycloalkenyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated, (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —NO$_2$, —CN, —N$_3$, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$— heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s), the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2$^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed.), "Design and Application of Prodrugs, Textbook of Drug Design and Development, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the Formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:

Ac for acetyl;
Boc$_2$O for di-tert-butyl-dicarbonate;
Boc for t-butoxycarbonyl;
Bz for benzoyl;
Bn for benzyl;
BocNHOH for tert-butyl N-hydroxycarbamate;
t-BuOK for potassium tert-butoxide;
BOP for (benzotriazol-1-yloxy)tris(dimethylamino)phosphonium Hexafluorophosphate;
Brine for sodium chloride solution in water;
CDI for carbonyldiimidazole;
CH$_2$Cl$_2$ for dichloromethane;
CH$_3$ for methyl;
CH$_3$CN for acetonitrile;
Cs$_2$CO$_3$ for cesium carbonate;
dba for dibenzylidene acetone;
dppb for diphenylphosphino butane;
dppe for diphenylphosphino ethane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or (i-Pr)$_2$EtN for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
Et$_2$O for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
K$_2$CO$_3$ for potassium carbonate;
MeOH for methanol;
Ms for mesyl or —SO$_2$—CH$_3$;
Ms$_2$O for methanesulfonic anhydride or mesyl-anhydride;
NaHCO$_3$ for sodium bicarbonate or sodium hydrogen carbonate;
Na$_2$CO$_3$ sodium carbonate;
NaOH for sodium hydroxide;
Na$_2$SO$_4$ for sodium sulfate;
NaHSO$_3$ for sodium bisulfite or sodium hydrogen sulfite;
Na$_2$S$_2$O$_3$ for sodium thiosulfate;
NH$_2$NH$_2$ for hydrazine;
NH$_4$HCO$_3$ for ammonium bicarbonate;
NH$_4$Cl for ammonium chloride;
NMMO for N-methylmorpholine N-oxide;
NaIO$_4$ for sodium periodate;
OH for hydroxy;
OsO$_4$ for osmium tetroxide;
TEA or Et$_3$N for triethylamine;
TFA for trifluoroacetic acid;
THF for tetrahydrofuran;
TPP or PPh$_3$ for triphenylphosphine;
Ts for tosyl or —SO$_2$—C$_6$H$_4$—CH$_3$;
Ts$_2$O for tolylsulfonic anhydride or tosyl-anhydride;
TsOH for p-tolylsulfonic acid;
Pd for palladium;
Ph for phenyl;
Pd$_2$(dba)$_3$ for tris(dibenzylideneacetone) dipalladium (0);
Pd(PPh$_3$)$_4$ for tetrakis(triphenylphosphine)palladium (0);
TBS for tert-butyl dimethylsilyl;
TMS for trimethylsilyl;
TMSCl for trimethylsilyl chloride;
CsA for cyclosporine A.

Synthetic Methods

The compounds and processes of the present invention will be better understood in connection with the following synthetic schemes that illustrate the methods by which the compounds of the invention may be prepared.

The novel cyclosporine analogues of the present invention are derived from cyclosporine A. As shown in Scheme 1, Compound of formula (1-1), which is prepared by selective removal of two amino acids in position three and four of cyclosporine according to the procedure described in WO 2010/088573, is reacted with Boc$_2$O in CH$_2$Cl$_2$ followed by the acetylation by reacting with acetic anhydride, optionally in the presence of pyridine or DMAP in CH$_2$Cl$_2$ to give compound of formula (1-2). Compound of formula (1-2) is converted to the compound of formula (1-3) by acidic Boc deprotection. The acid can be selected from, but not limited to, TFA, HCl in dioxane, methanesulfonic acid. A more through discussion of the procedures, reagents and conditions for protection and deprotection is described in literature, for example, by T. W. Greene and P. G. M. Wuts in "*Protective Groups in Organic Synthesis*" 3$^{rd}$ ed., John Wiley & Son, Inc., 1999. Five consecutive Edman degradation of (1-3) gave the key intermediate of formula (1-4).

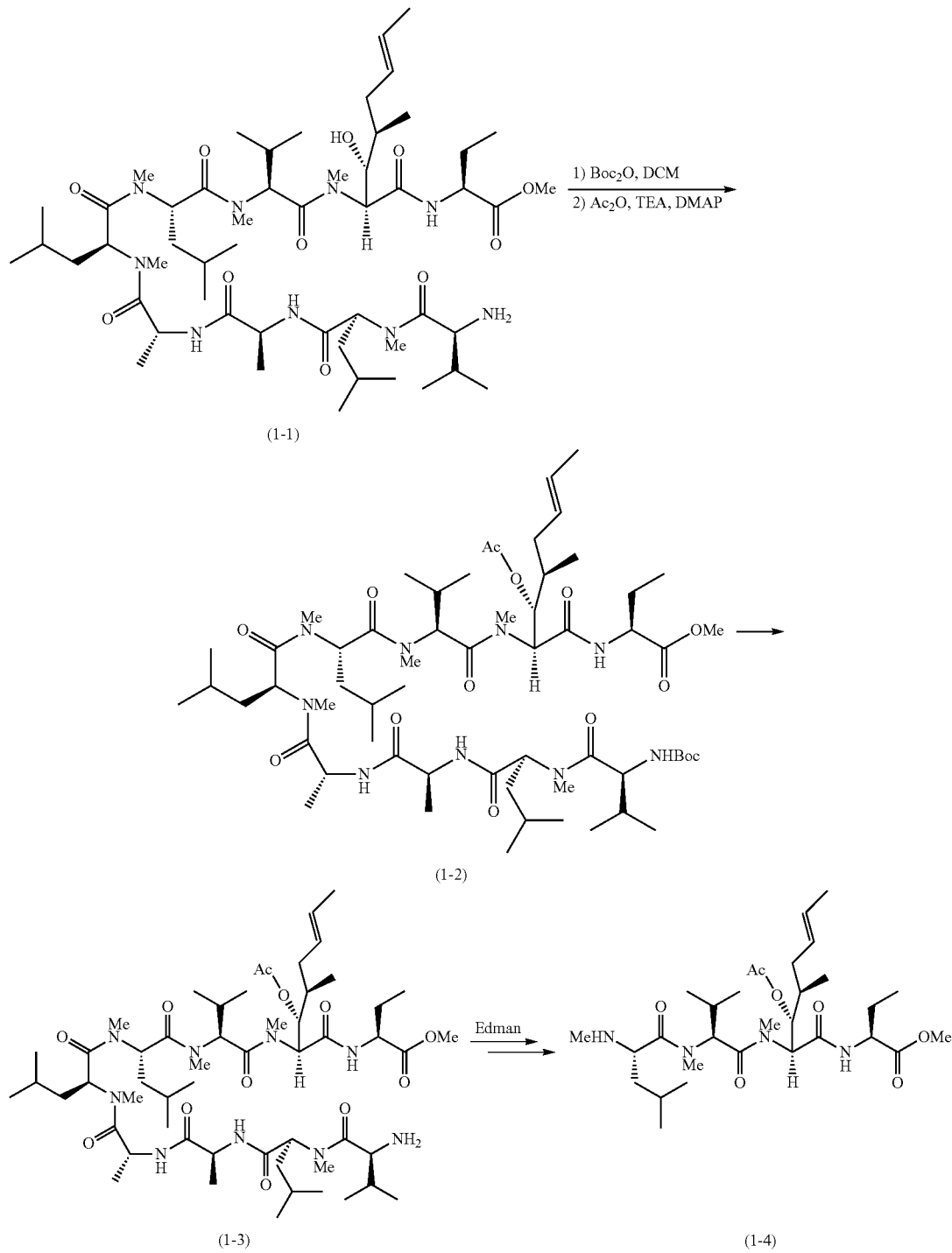

Scheme 1

Scheme 2 illustrates a process of preparation of protected 4-hydroxy N-methyl leucine of formula (2-7). $P_1$ protected (S)-3-amino-γ-butyrolactone compound (2-1), herein $P_1$ is amino protecting group, such as but not limited to, Cbz, Boc, benzyl, acetyl, reacts with excess amount of methyllithium or Grignard reagent such as not limited to methylmagnesium-bromide in the presence of catalyst such as but not limited to cerium chloride (III), titanium tetraisopropoxide in aprotic solvent such as diethyl ether, THF, DME to provide dihydroxy compound of formula (2-2) according to the modified procedure from the account by Esposito, A.; Taddel, M. *J. Org. Chem.*, 2000, 65, 9245. Dihydroxy groups of the compound (2-2) are protected by silyl protection group ($P_2$) such as but not limited to TES, TBS, TMS, TIPS and TBDPS to provide the compound of formula (2-3). A more thorough discussion of the procedures, reagents and conditions for protecting hydroxyl group is described in literature, for example, by T. W. Greene and P. G. M. Wuts in "*Protective Groups in Organic Synthesis*" $3^{rd}$ ed., John Wiley & Son, Inc., 1999. N-methylation on protected diol (2-3) (see the account, i.e., Wipf, P.; Wang, Z., *Org. Lett.*, 2007, 9, 1605) using base such as but not limited to NaHMDS, NaH and methylating agent such as but not limited to iodomethane gave the compound of formula (2-4). Selective de-silylation of compound (2-4) is achieved by the reaction with desilylating reagent containing fluorine such as but not limited to HF.pyridine, TBAF, CsF or acidic condition such as diluted acetic acid, TFA to afford the primary alcohol compound of formula (2-5) in good yield. Protected N-methyl 4-hydroxyleucine of formula (2-7) is obtained directly from the alcohol compound of formula (2-5) or via the intermediate aldehyde compound of formula (2-6). Direct oxidation conditions from primary alcohol to carboxylic acid are described in the accounts, Burgess, K.; Liu, L. T.; Pal, B. *J. org. Chem.*, 1993, 58, 4758; Mori, K.; Ebata, T., *Tetrahedron Lett.*, 1986, 42, 4413; Hanessian, S.; Del Valle, J. R.; Xue, Y.; Blomberg, N., *J. Am. Chem. Soc.*, 2006, 128, 10491; Zhao, M.; Li J.; Song, Z.; Desmond, R.; Tschaen, D. M.; Grabowski, E. J. J.; Reider, P. J.; *Tetrahedron Lett.*, 1998, 39, 5323. These procedures use the mild oxidizing reagents such as but not limited to $RuCl_3$, $H_5IO_6$ and $CrO_3$. In an alternative way, the primary alcohol compound (2-5) was converted to the aldehyde compound (2-6) by oxidation conditions such as but not to limited to Swern oxidation, Dess-Martin oxidation and Corey-Kim oxidation. The aldehyde compound (2-6), thus, was further oxidized to the protected N-methyl 4-hydroxyleucine (2-7) by the mild oxidation condition such as but no limited to the condition using sodium phosphate dibasic and sodium chlorite (see, i.e., Taylor, C. M.; Barker, W. D.; Weir, C. A.; Park, J. H., *J. Org. Chem.*, 2002, 67, 4466).

Scheme 3 illustrates a process of the invention for the preparation of compounds according to the invention. Thus the compound of formula (1-4) is coupled with a protected N-methyl 4-hydroxy leucine (2-7), herein P1 is Boc and P2 is TES, followed by acidic deprotection to give the compound of formula (3-1). The coupling regent can be selected from, but not limited to, DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF or THF. The reaction temperature can vary from 0° C. to about 50° C. The acid can be selected from, but not limited to, TFA, HCl in dioxane, methanesulfonic acid. A more detailed discussion of the procedures, reagents and conditions for removing protecting groups is described in literature, for example, by T. W. Greene and P. G. M. Wuts in "*Protective Groups in Organic Synthesis*" $3^{rd}$ ed., John Wiley & Son, Inc., 1999. Then the compound of formula (3-1) is coupled with Boc protected D-alanine to give the compound of formular (3-2). Another coupling of the compound of formular (3-2) with the Fmoc protected tripeptide compound of formular (3-3) to give the compound of formular (3-4).

The Fmoc protected tripeptides of formula (3-4) can be prepared by the method described in Hu, T. and Panek, J. S.; *J. Am. Chem. Soc.* 2002, 124, 11372.

The compound of formula (3-4) is converted to the compound of formula (3-5) with sodium methoxide in methanol. Then, the compound of formula (3-5) is coupled with a protected dipeptide of the formula (3-6) to give the compound of formula (3-7). The coupling regent can be selected from, but not limited to, DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF or THF. The reaction temperature can vary from 0° C. to about 50° C.

The protected dipeptides of formula (3-6) can be prepared by the method described in Hu, T. and Panek, J. S.; *J. Am. Chem. Soc.* 2002, 124, 11372.

The compound of formula (3-7) is converted to the compound of formula (3-8) via an alkaline hydrolysis in protic solvent, followed by acidic Boc deprotection. For acidic deprotection, the acid can be selected from, but not limited to, Scheme 2

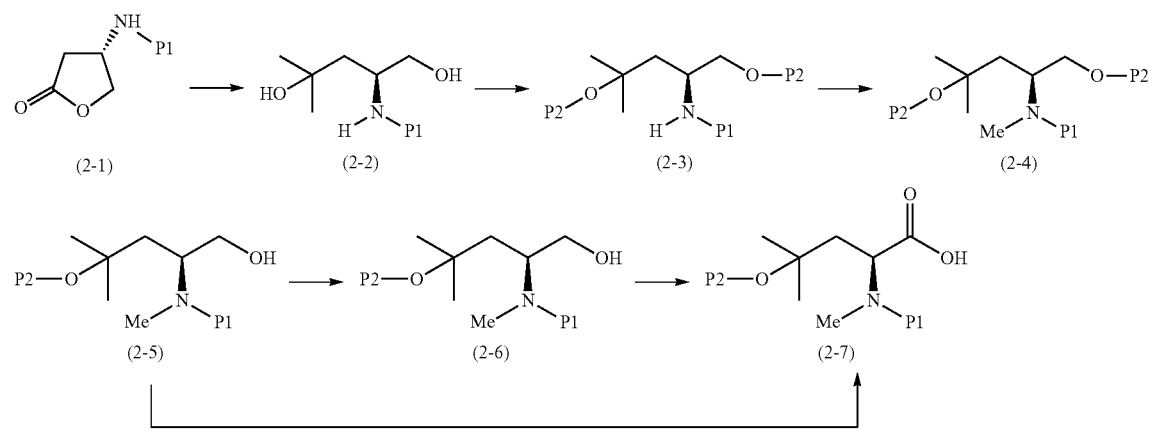

TFA, HCl in dioxane, methanesulfonic acid. A more detailed discussion of the procedures, reagents and conditions for removing protecting groups is described in literature, for example, by T. W. Greene and P. G. M. Wuts in "*Protective Groups in Organic Synthesis*" 3$^{rd}$ ed., John Wiley & Son, Inc., 1999.
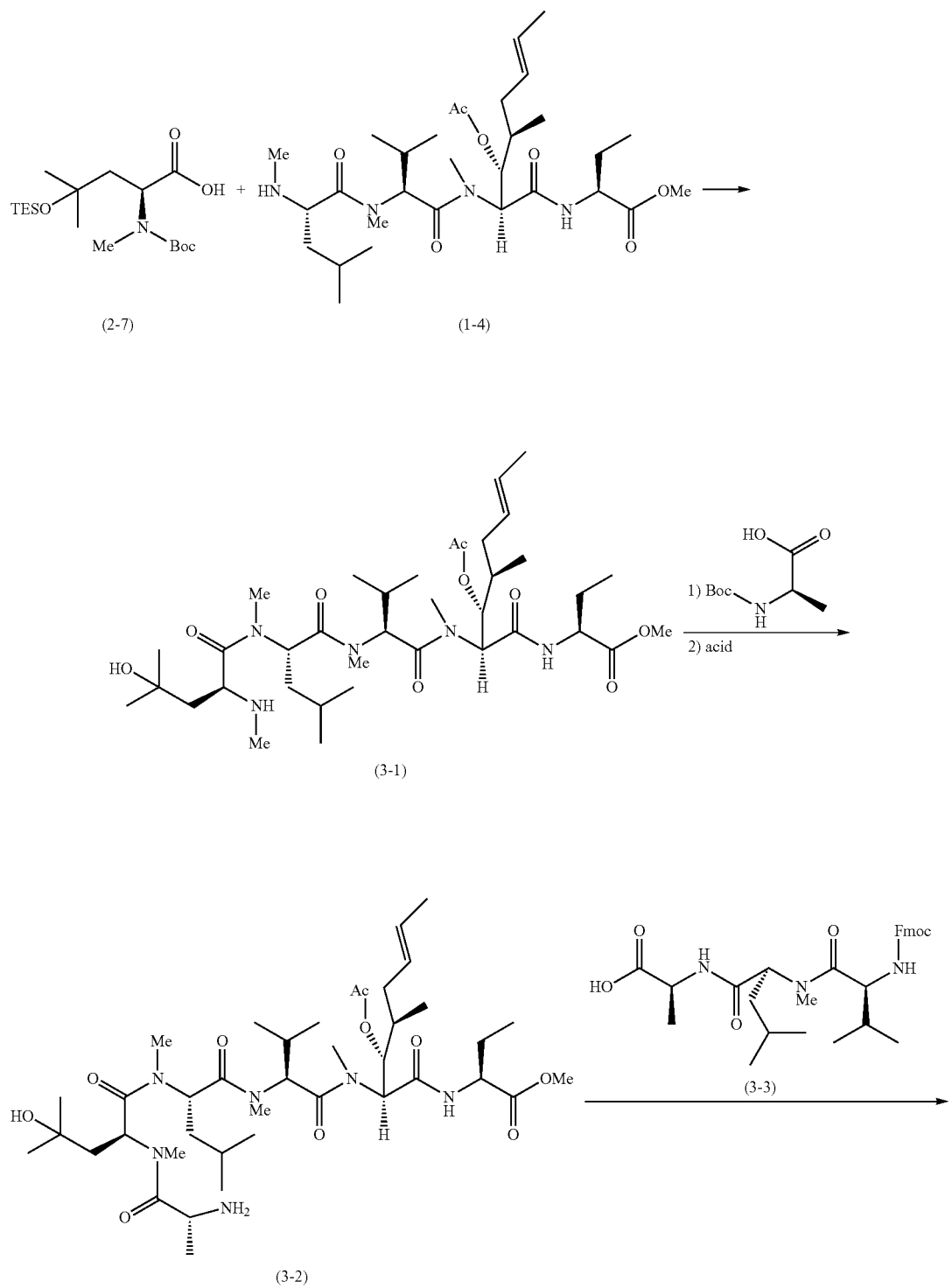
Scheme 3

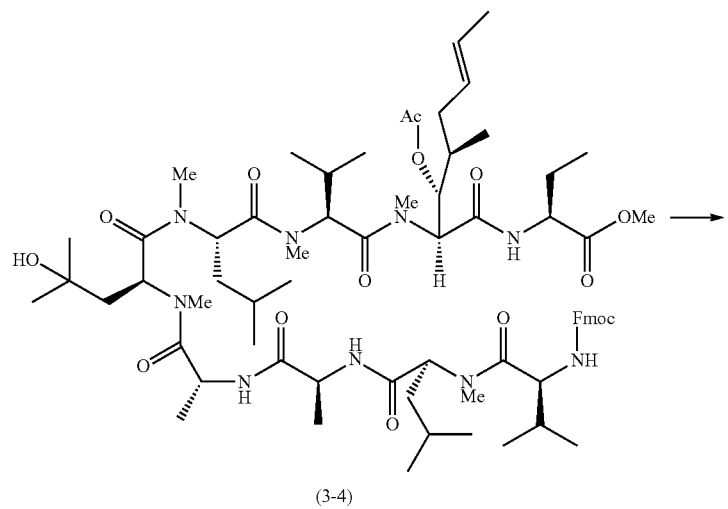
(3-4)
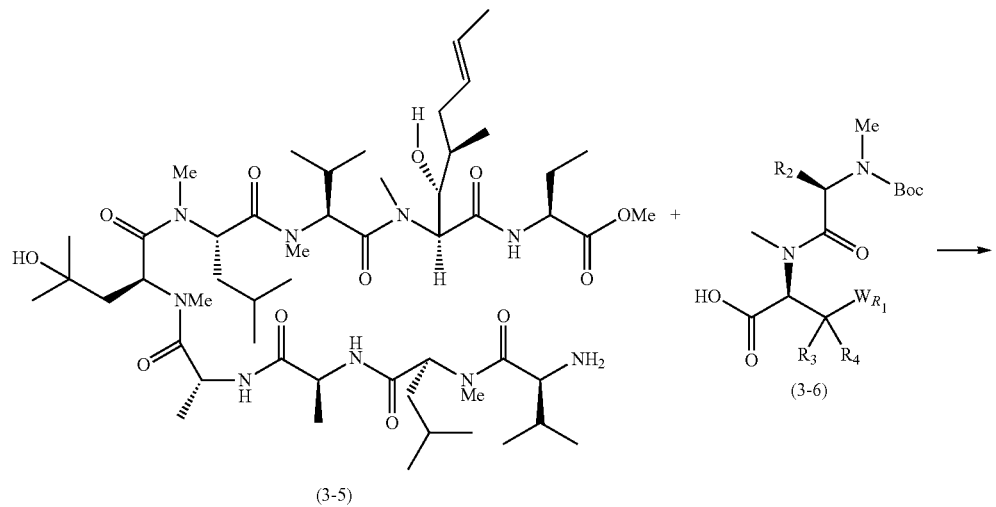
(3-5)     (3-6)
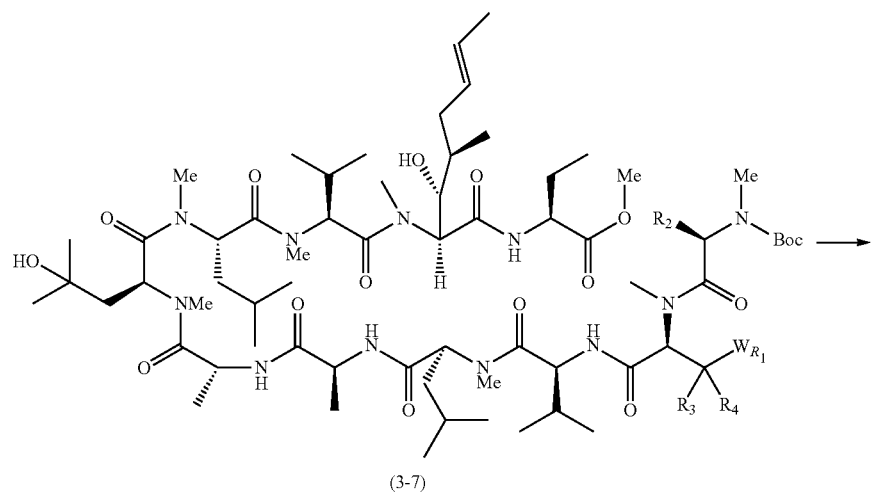
(3-7)

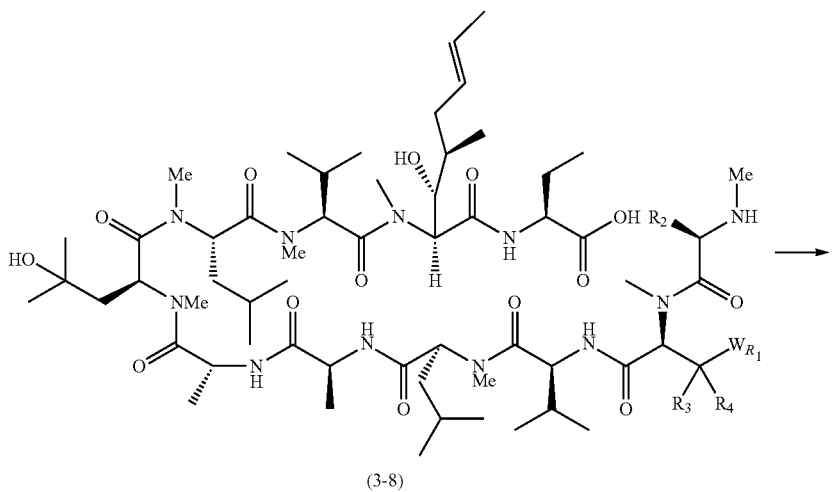

(3-8)

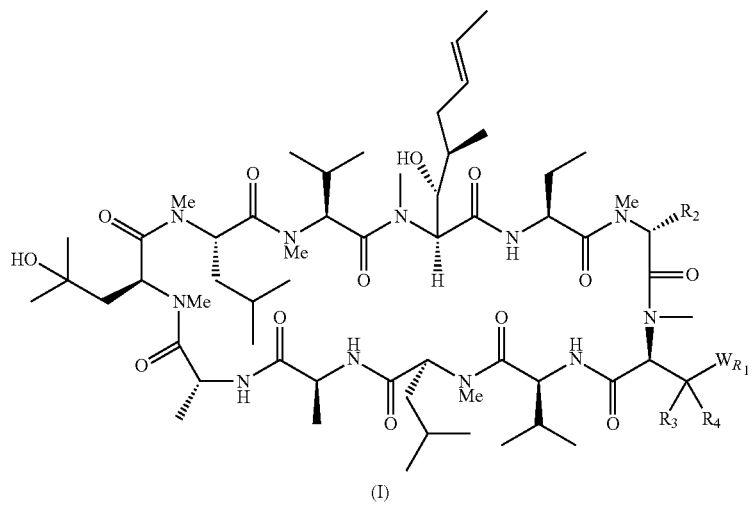

(I)

For alkaline hydrolysis, the representative alkali compounds include lithium hydroxide, sodium hydroxide, potassium hydroxide, and the like. Suitable solvents include, but are not limited to, methanol, ethanol, isopropanol, butanol, THF, 1,4-dioxane and mixtures there of. The reaction temperature is preferably 0° to 35° C. Compound of formula (I) is prepared by intramolecular amide formation reaction. The regent can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF and THF. The reaction temperature can vary from 0° C. to about 50° C.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula IV

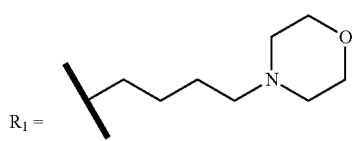

$R_1 =$

Preparation of Compound of Formular (1-4)

Step 1a

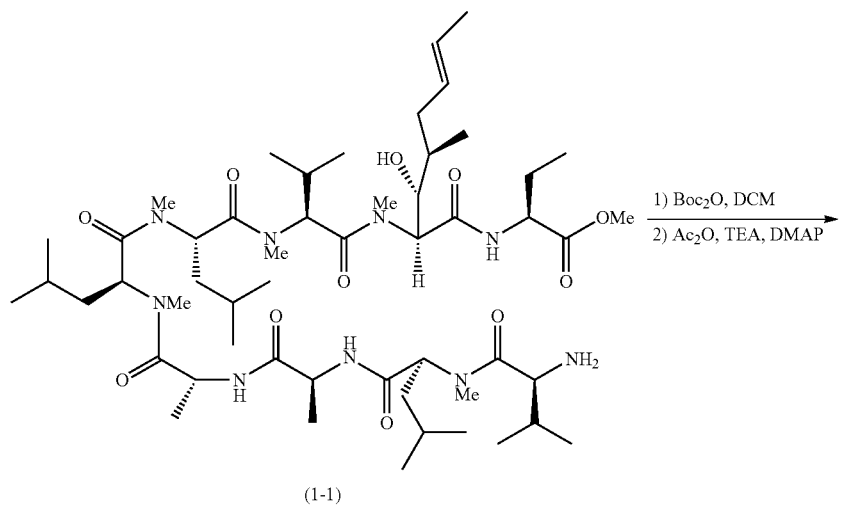

(1-1)

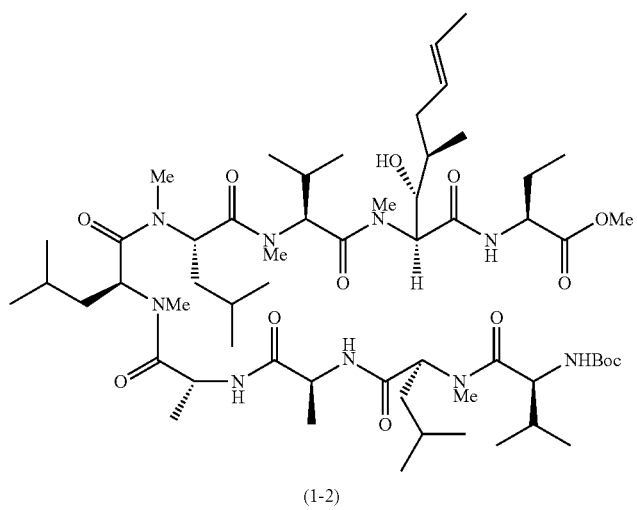

(1-2)

To a 250 mL round-bottomed flask were added the compound of formula (1-1) (20.7 g, 1.0 equiv., 20 mmol), DCM (52 mL, 2.5 Vol.), and Boc$_2$O (4.8 g, 1.1 equiv., 22 mmol) respectively and the solution was stirred at room temperature for 2.5 h. Acetic anhydride (3.06 g, 2.84 mL, 1.5 equiv., 30 mmol), triethylamine (4.05 g, 5.58 mL, 2.0 equiv., 40 mmol), DMAP (244 mg, 0.1 equiv., 2 mmol) were added respectively and the resulting mixture was stirred at room temperature for 16 h. Quenched with MeOH (3 mL) slowly, stirred for 15 min at room temperature. Diluted with MTBE (300 mL), and the organic layer was washed with H$_2$O (150 mL), Sat. NaHCO$_3$ (150 mL), and brine (150 mL) sequentially. Dried over Na$_2$SO$_4$, filtered and the solvent was removed to give a white solid 23.2 g, 98.5% Yield.

ESI MS m/z=1178.8 [M+H]$^+$.

Step 1b

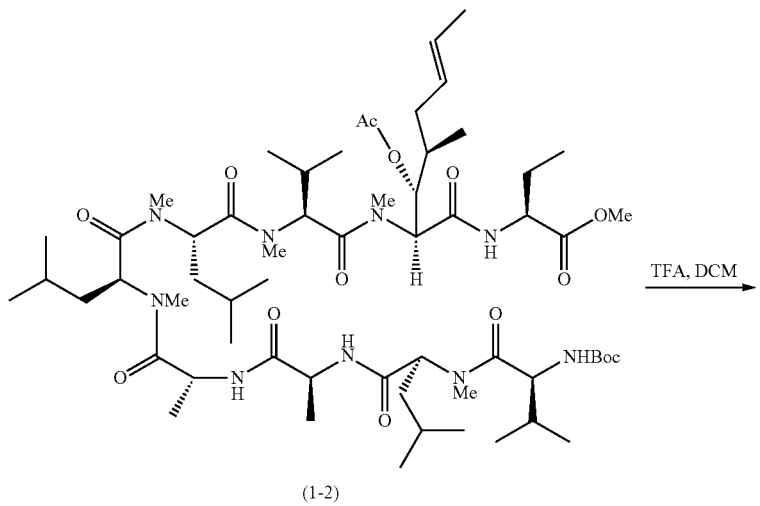

(1-2)

(1-3)

To a 2 L 3-necked round-bottomed flask were added the compound of formula (1-2) (40.3 g, 34.2 mmol), DCM (406 mL) and the solution was cooled to 0° C. under $N_2$ followed by the addition of TFA (203 mL) during 0.5 h. After stirred at 0° C. for 1.5 h, the yellowish solution was diluted with cold DCM (400 mL) and then quenched with 2.3 M aq. $K_2CO_3$ solution (600 mL) slowly during 40 min. The organic layer was separated, washed with Sat. $NaHCO_3$/half brine (600 mL, ⅓). Dried over $Na_2SO_4$, filtered, and the solvent was removed to give a white solid 34.5 g, 93.5% Yield.

ESI MS m/z=1078.8 $[M+H]^+$.

Step 1c

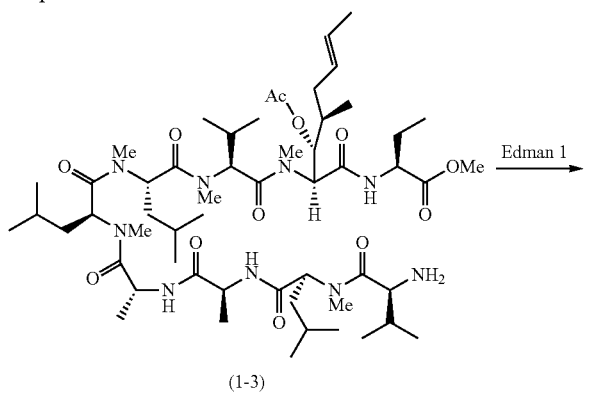

(1-3)

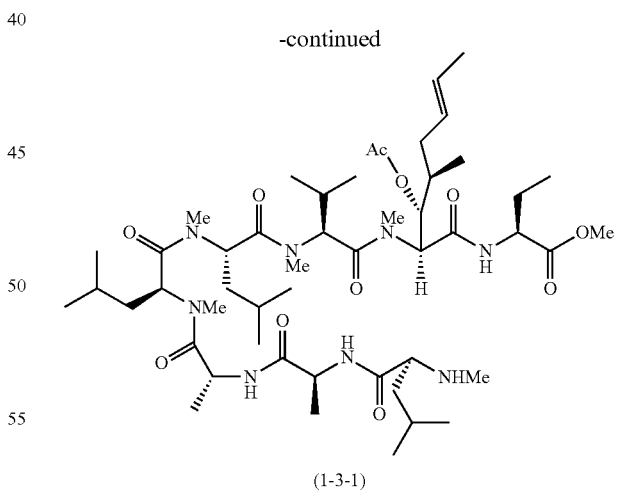

(1-3-1)

To a 1 L round-bottomed flask were added the compound of formula (1-3) (34.5 g, 31.9 mmol), THF (200 mL), phenyl isothiocyanate (4.4 g,), N-methyl morpholine (877 μL) and the resulting mixture was stirred at room temperature for 2 h. Pyrrolidine (533 μL) was added and the solution was stirred for 0.5 h at room temperature. The solvent was removed and the residue was purified by Combiflash (750 g $SiO_2$, Acetone/Hexanes: 10~70%) to give a white solid 32.7 g. To this white solid was added DCM (170 mL), TFA (36.4 mL,) and the resulting mixture was stirred at room temperature for 2.5 h. Quenched with MeOH (60 mL), stirred at room temperature for 0.5 h. The solvent was removed and the residue was diluted with EtOAc (600 mL), washed with Sat. NaHCO₃ (200 mL) and brine (200 mL) respectively. Dried over Na₂SO₄, filtered, the sovent was removed and the residue was purified by Combiflash (330 g SiO₂, MeOH/DCM: 0-10%) to give the compound of formula (1-3-1) as a white solid 20.6 g.

ESI MS m/z=979.7 [M+H]⁺.

Step 1d

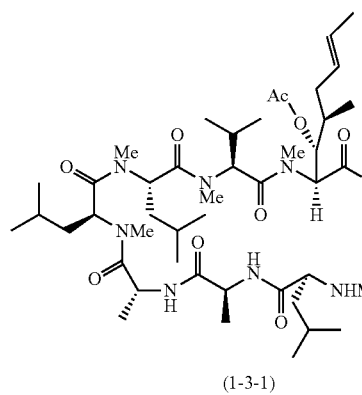

(1-3-1)

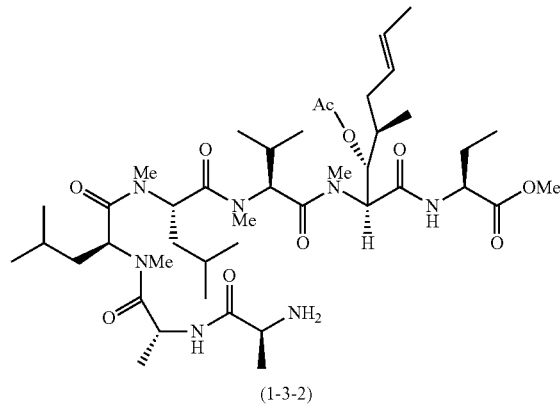

(1-3-2)

To a 1 L round-bottomed flask containing the compound of formula (1-3-1) (20.5 g, 20.9 mmol) were added THF (123 mL), phenyl isothiocyanate (2.55 mL, 21.4 mmol), N-methylmorpholine (574 μL) and the resulting mixture was stirred at room temperature for 2 h. Another portion of phenyl thioisocyanate (0.5 mL) was added. After 40 min, DMAP (0.2 equiv.) was added and the reaction was stirred for another 2. Quenched with pyrrolidine (349 μL) and stirred for 0.5 h atroom temperature. The solvent was removed and the residue was purified by Combiflash (Ace/Hex: 10~100%) to give a white solid 17.2 g. To this white solid were added DCM (85 mL), TFA (9.15 mL) and reaction mixture was stirred at room temperature for 1 h before quenched with MeOH (34 mL). After stirred at room temperature for 40 min, the solvent was removed and the residue was diluted with EtOAc (500 mL). Washed with Sat. NaHCO₃ solution/Sat. Na₂CO₃ solution (200 mL, 1:1) and brine (200 mL) respectively, then dried over Na₂SO₄, filtered and the solvent was removed. The residue was purified by Combiflash (220 g SiO₂, MeOH/DCM: 0-10%) to give the compound of formula (1-3-2) as a white solid 12.1 g, 92.6% yield.

ESI MS m/z=852.6 [M+H]⁺.

Step 1e

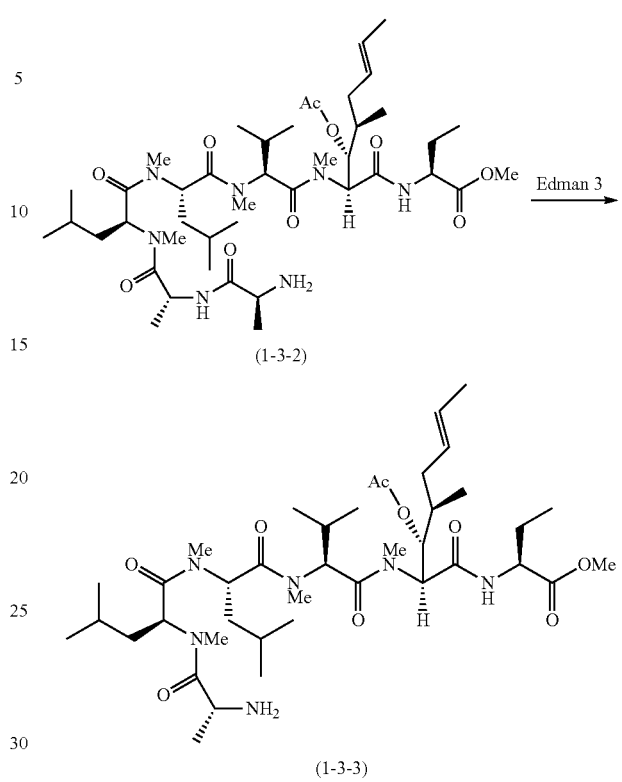

The compound of formula (1-3-2) (12 g) was converted to the compound of formula (1-3-3) using similar Edman degradation conditions as used in step 1d to give a white solid 9.2 g, 83.6% yield.

ESI MS m/z=781.5 [M+H]⁺.

Step 1f

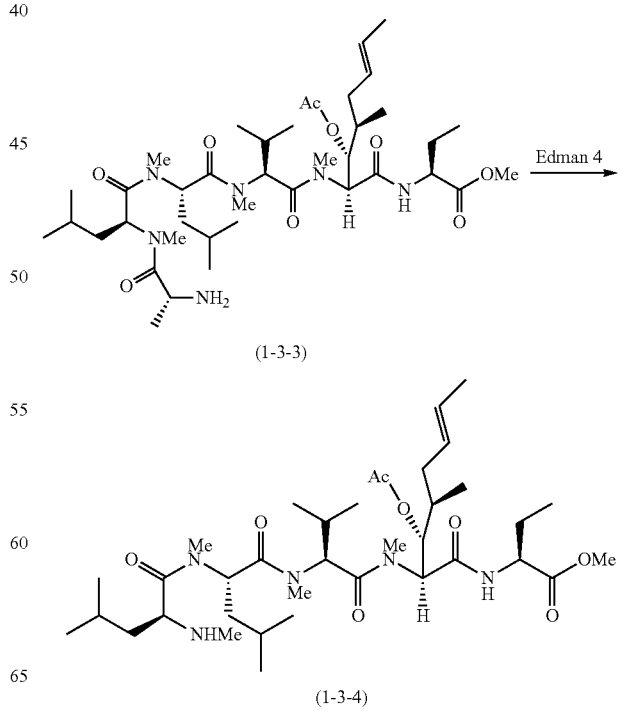

The compound of formula (1-3-3) (9.1 g) was converted to the compound of formula (1-3-4) using similar Edman degradation conditions as used in step 1d to give a white solid 7.2 g, 87% yield.

ESI MS m/z=710.5 [M+H]⁺.

Step 1g:

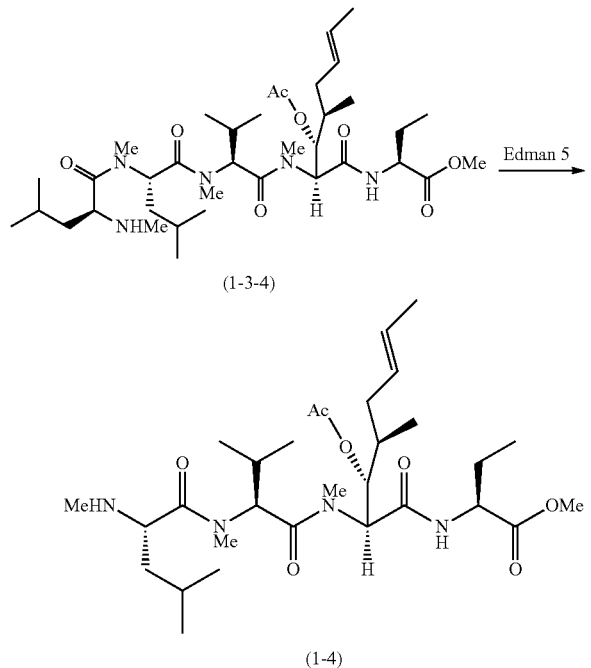

The compound of formula (1-3-4) (7.2 g) was converted to the compound of formula (1-4) using similar Edman degradation conditions as used in step 1d to give a white solid 4.7 g, 80% yield.

ESI MS m/z=583.5 [M+H]⁺.

Preparation of Protected 4-hydroxyleucine (2-7)

Step 2a

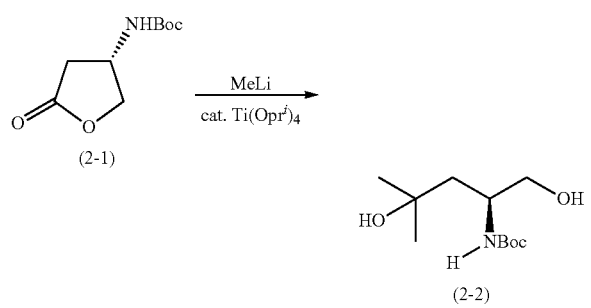

To a mixture of compound (2-1) (7.0 g, 34.29 mmol) in Et$_2$O-THF (2:1, 210 mL) was added Ti($^i$OPr)$_4$ (5.2 mL, 0.5 eq.), followed by addition of methyllithium (109 mL, 1.6M in Et$_2$O, 5 eq.) at 15° C. for 1.5 hr. The reaction was slowly allowed to warm to room temperature and stirred for overnight. It was cooled to 0° C. and quenched by addition of saturated aqueous NH$_4$Cl sol'n (70 mL), extracted with ethyl acetate (280 mL) and separated. The aqueous layer was neutralized with 10% citric acid (~pH7) and extracted with ethyl acetate (3×280 mL). The combined organic layer was washed with saturated aqueous NaHCO$_3$ sol'n (100 mL) and brine, successively. The organic layer was dried over Na$_2$SO$_4$, filtered and evaporated to dryness. The residue was purified by silica gel column chromatography with 0~30% acetone in hexanes to give the compound (2-2) (3.47 g) as a colorless oil.

MS: (ESI) m/z (M+Na) 256.22.

Step 2b

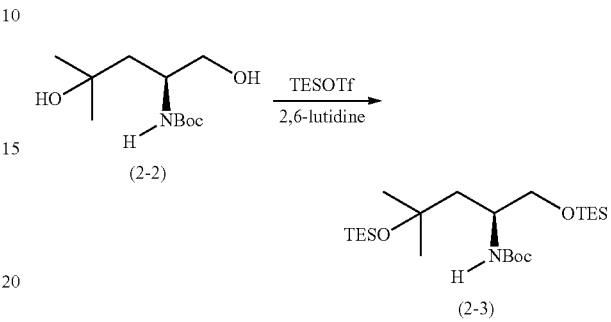

To a mixture of compound (2-2) (1.22 g, 5.23 mmol) and 2,6-lutidine (1.8 mL, 3.0 eq.) in dry dichloromethane (26 mL) was added TESOTf (2.6 mL, 2.2 eq.) at −50° C. and slowly allowed to warm to 0° C. for 30 min., which was further allowed to warm to room temperature for 30 min and stirred for 1.5 hr. It was diluted with dichloromethane (20 mL), washed with saturated aqueous NaHCO$_3$ sol'n (10 mL) and brine, successively. The organic layer was dried over Na$_2$SO$_4$, filtered and evaporated to dryness. The residue was purified by silica gel column chromatography with 0~10% ethyl acetate in hexanes to give the compound (2-3) (2.32 g) as a colorless oil.

MS: (ESI) m/z (M+Na) 484.39.

Step 2c

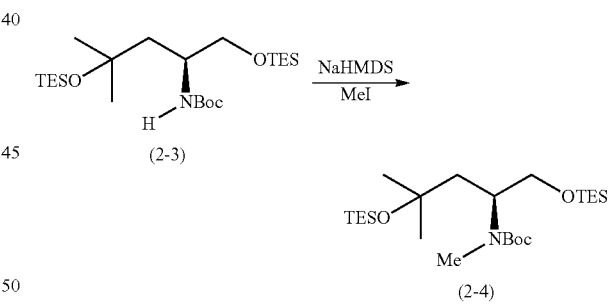

To a mixture of compound (2-3) (6.355 g, 13.76 mmol) in dry THF (105 mL) was added sodium bis(trimethylsilyl)amide (30.3 mL, 1M in THF, 2.2 eq.) at 0° C. and stirred for 30 min. Then, iodomethane (5.14 mL, 6 eq.) was added to the reaction and slowly allowed to warm to room temperature for 13 hrs. The reaction was cooled to 0° C., quenched by addition of saturated aqueous NH$_4$Cl solution (12 mL) and H$_2$O (10 mL), which was evaporated off. The residue was extracted with ethyl acetate (3×50 mL). The combined organic layer was washed with brine, dried over Na$_2$SO$_4$, filtered and evaporated to dryness. The residue was purified by silica gel column chromatography with 0~10% ethyl acetate in hexanes to give the compound (2-4) (6.328 g) as a colorless oil.

MS: (ESI) m/z (M+Na) 498.36.

Step 2d

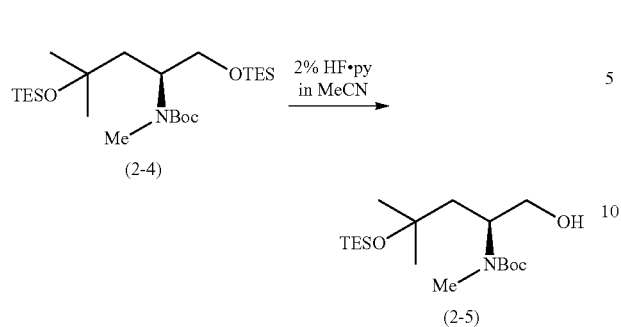

A mixture of compound (2-4) (3.393 g, 7.13 mmol) in acetonitrile (10 mL) was cooled to 0° C., treated with 2% HF.pyridine in acetonitrile (60 mL, pre-chilled at 0° C.) and stirred at 0° C. for 15 min. The reaction was quenched by addition of saturated aqueous NaHCO$_3$ sol'n (30 mL) and evaporated off. The residue was extracted with ethyl acetate (2×50 mL). The combined organic layer was washed with brine, dried over Na$_2$SO$_4$, filtered and evaporated to dryness. The residue was purified by silica gel column chromatography with 0~20% acetone in hexanes to give the compound (2-5) (2.273 g) as a colorless oil.

MS: (ESI) m/z (M+H) 362.36, (M+Na) 384.35.

Step 2e

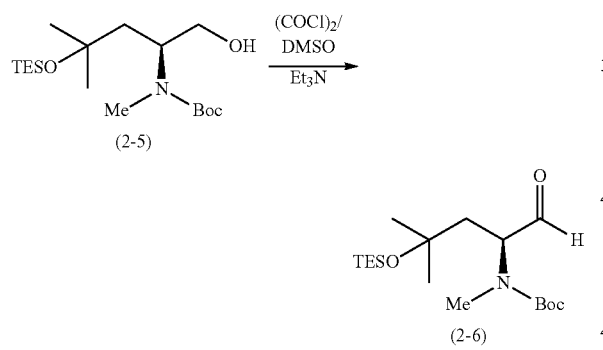

To a mixture of oxalyl chloride (1.314 ml, 2.4 eq.) in dry dichloromethane (80 mL) was dropwise added dimethyl sulfoxide (2.14 mL, 4.8 eq.) in dry dichloromethane (25 mL) at −78° C. and stirred for 20 min. the compound of (2-5)(2.27 g, 6.28 mmol) in dry dichloromethane (30 mL) was dropwise added to the reaction mixture at −78° C., stirred for 1 hr and slowly allowed to −40° C. for 1.5 hr. Then, triethylamine (5.25 mL, 7 eq.) was added to the reaction and stirred at 0° C. for 20 min. The reaction was quenched by addition of saturated aqueous NH$_4$Cl solution (10 mL) and separated. The organic layer was washed with H$_2$O and brine, successively. The organic layer was dried over Na$_2$SO$_4$, filtered and evaporated to dryness. The residue was purified by silica gel column using 0-10% ethyl acetate in hexanes to give the compound (2-6) (1.066 g) as a colorless oil.

$^1$H-NMR (CDCl$_3$) δ: 9.56 (—CHO).

MS: (ESI) m/z (M+H) 360.36

Step 2f

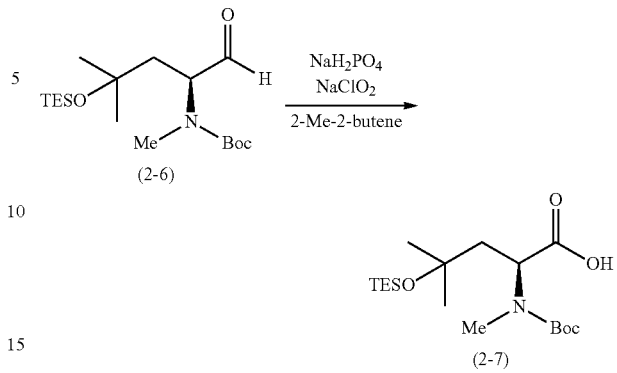

To a mixture the compound (2-6) (1.066 g, 2.96 mmol) and sodium phosphate monobasic (0.356 g, 1 eq.) and 2-methyl-2-butene (6.5 mL, 2M in THF, 4.4 eq.) in tert-butanol-distilled water (3:1, 24 mL) was added sodium chlorite (1.14 g, ~80%, 3.4 eq.) at room temperature and stirred for 30 min. The reaction was diluted with dichloromethane (100 mL) washed with saturated aqueous NH$_4$Cl solution (20 mL), H$_2$O and brine, successively. The organic layer was dried over Na$_2$SO$_4$, filtered and evaporated to dryness. The residue was purified by silica gel column chromatography with 0~20% acetone in hexanes to give the compound (2-7) (0.249 g) as a colorless oil.

MS: (ESI) m/z (M+H) 398.33.

Preparation of Example 1

Step 3a

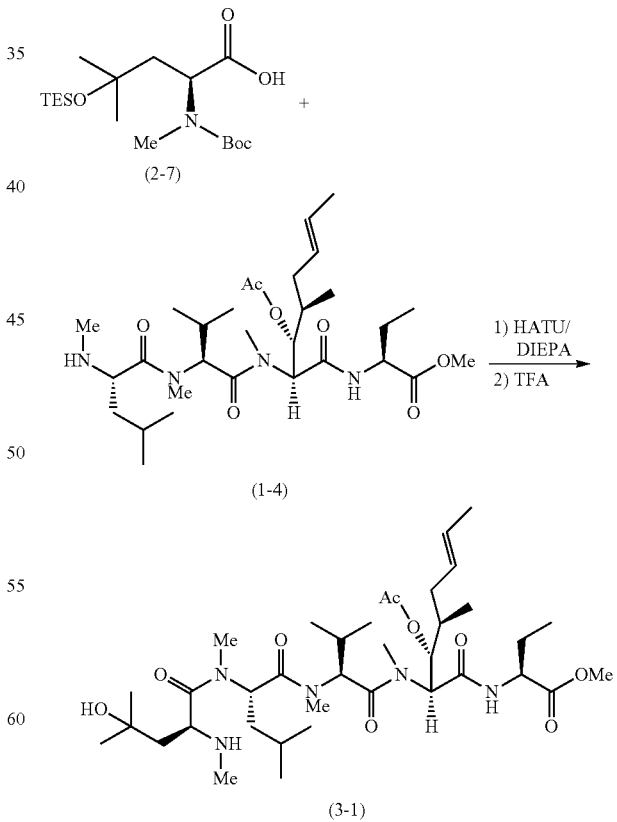

To a mixture of the compound (2-7) (0.49 g, 1.3 mmol), the compound (1-4) (0.76 g, 1.eq) and N,N-diisopropylethylamine (0.45 mL, 2 eq.) in dry acetonitrile (6.5 mL) was added HATU (0.595 g, 1.2 eq.) at room temperature and stirred for 15 hrs. The reaction was diluted with ethyl acetate (50 mL), washed with saturated aqueous NaHCO$_3$ sol'n (5 mL) and brine, successively. The organic layer was dried over Na$_2$SO$_4$, filtered and evaporated to dryness. The residue was purified by silica gel column chromatography with 0~20% acetone in hexanes to give the coupling product (0.857 g) as a white foam.

MS: (ESI) m/z (M+H) 940.65, (M+Na) 962.63.

The above coupling product (854 mg, 0.91 mmol) was dissolved in dry dichloromethane (11.1 mL), cooled to 0° C. and treated with trifluoroacetic acid (6.3 mL, 90 eq.) and stirred at 0° C. for 2 hrs. The reaction was poured into cold saturated aqueous NaHCO$_3$ sol'n (50 mL) with vigorous stirring and separated. The aqueous layer was extracted with dichloromethane (2×15 mL). The combined organic layer was washed with brine, dried over Na$_2$SO$_4$, filtered and evaporated to dryness. The residue was purified by silica gel column chromatography with 0~8% methanol in dichloromethane to give the compound (3-1) (0.596 g) as a white foam.

MS: (ESI) m/z (M+H) 726.58, (M+Na) 748.58.

Step 3b

To a mixture of the compound (3-1) (0.594 g, 0.818 mmol), Boc-D-alanine (0.31 g, 2 eq.) and N,N-diisopropylethylamine (0.428 mL, 3 eq.) in dry dichloromethane (2.1 mL) was added HATU (0.778 g, 2.5 eq.) at 14° C. and stirred at room temperature for 11 hrs. The reaction was diluted with dichloromethane (30 mL), washed with saturated aqueous NaHCO$_3$ sol'n (5 mL). The aqueous layer was extracted with dichloromethane (2×10 mL). The combined organic layer was washed with saturated aqueous NaHCO$_3$ sol'n (5 mL), H$_2$O and brine, successively. The organic layer was dried over Na$_2$SO$_4$, filtered and evaporated to dryness. The residue was purified by silica gel column chromatography with 0~30% acetone in hexanes to give the coupling product (0.676 g) as a white foam.

MS: (ESI) m/z (M+H) 897.47, (M+Na) 919.45.

The above coupling product (673 mg, 0.75 mmol) was dissolved in dry dichloromethane (9.2 mL), cooled to 0° C. and treated with trifluoroacetic acid (5.2 mL, 90 eq.) and stirred at 0° C. for 110 min. The reaction was poured into cold saturated aqueous NaHCO$_3$ sol'n (50 mL) with vigorous stirring and separated. The aqueous layer was extracted with dichloromethane (2×10 mL). The combined organic layer was washed with brine, dried over Na$_2$SO$_4$, filtered and evaporated to give the compound (3-2) (0.564 g) as a white foam. MS: (ESI) m/z (M+H) 797.72, (M+Na) 819.68.

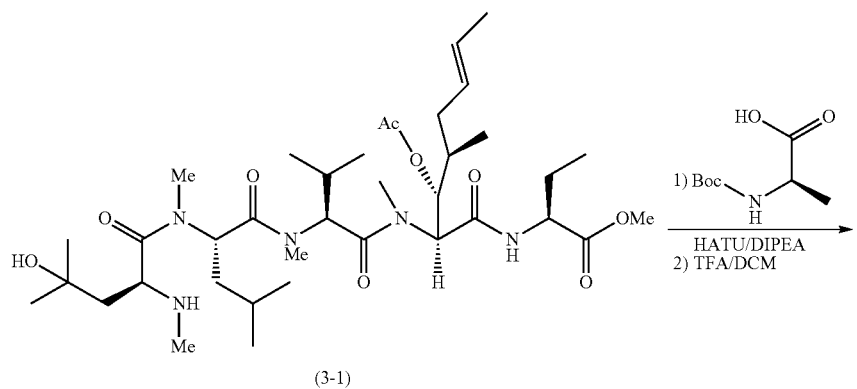

(3-1)

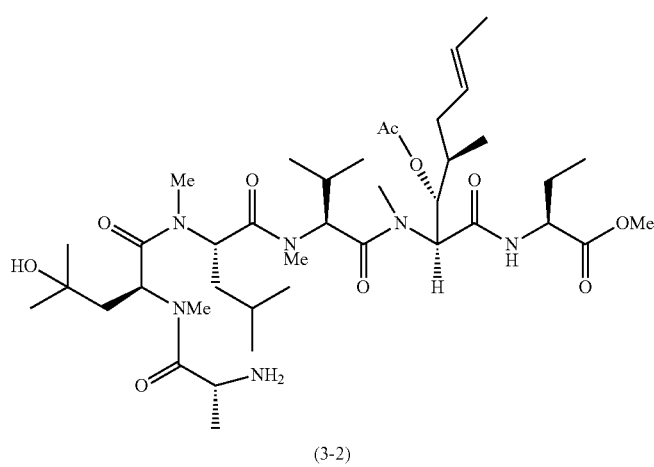

(3-2)

Step 3c

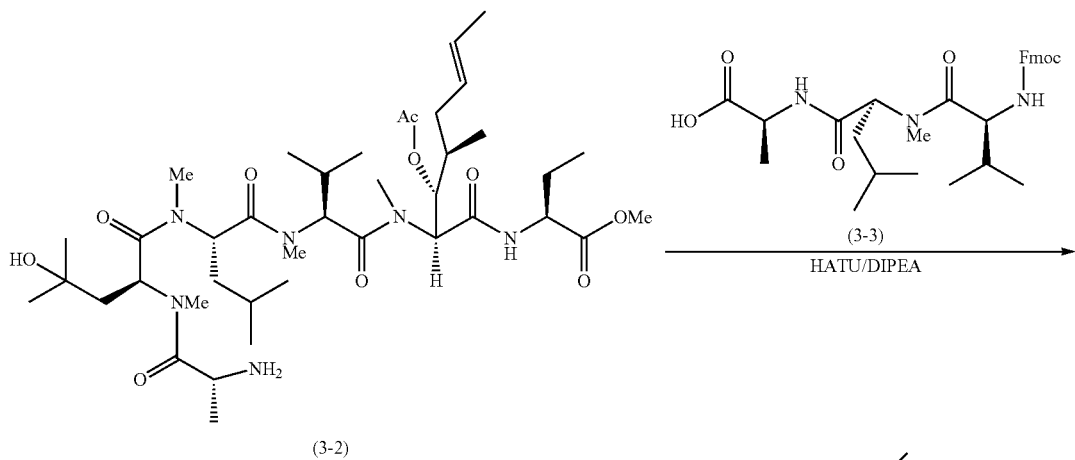

(3-2)

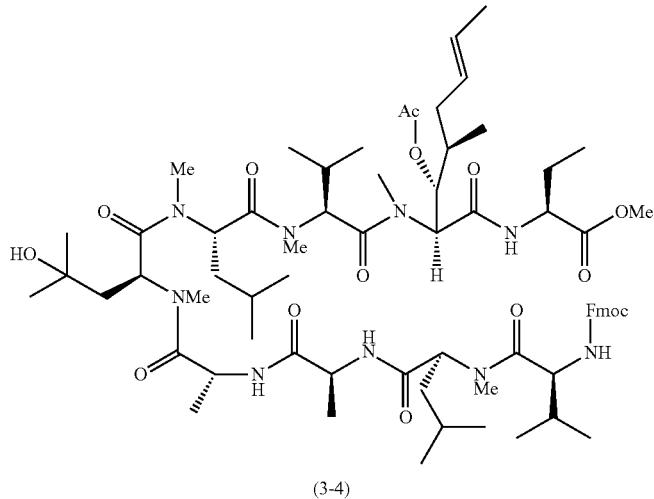

(3-4)

To a mixture of the compound (3-2) (0.562 g, 0.701 mmol), Fmoc protected tripeptide compound (3-3) (0.455 g, 1.2 eq.) and N,N-diisopropylethylamine (0.27 mL, 2.2 eq.) in dry dichloromethane (3.6 mL) was added HATU (0.375 g, 1.4 eq.) at 2° C. and stirred between 2 and 12° C. for 2 hrs. The reaction was diluted with dichloromethane (30 mL), washed with saturated aqueous $NaHCO_3$ (5 mL) and separated. The aqueous layer was extracted with dichloromethane (2×10 mL). The combined organic layer was washed with saturated aqueous $NaHCO_3$ sol'n (5 mL), $H_2O$ and brine, successively. The organic layer was dried over $Na_2SO_4$, filtered and evaporated to dryness. The residue was purified by silica gel column chromatography with 0~50% acetone in hexanes to give the compound (3-4) (0.855 g) as a white foam.

MS: (ESI) m/z (M+H) 1316.79, (M+Na) 1338.77.

Step 3d

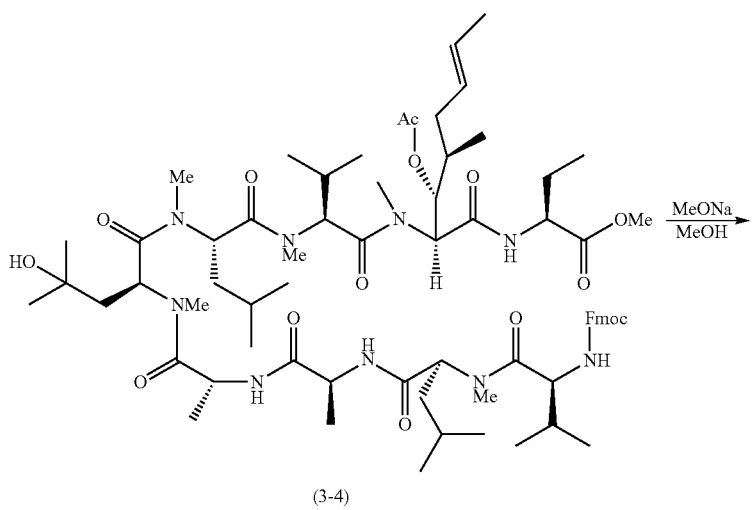

(3-4)

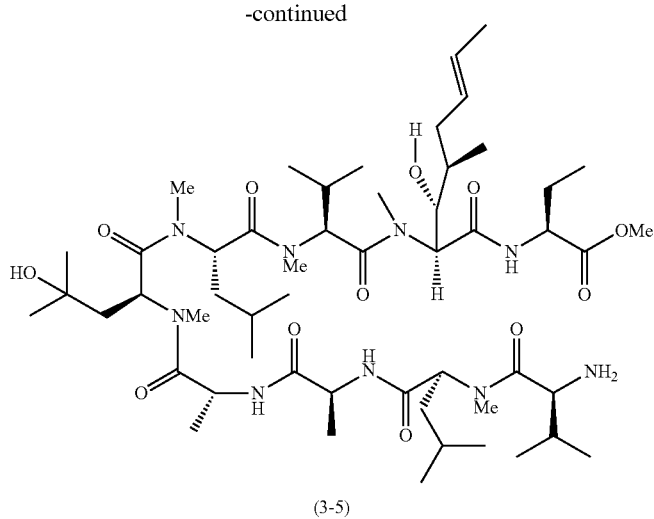

(3-5)

To a mixture of the compound (3-4) (0.854 g, 0.649 mmol) in dry methanol (7 mL) was dropwise added sodium methoxide (6.5 mL, 0.5M in methanol, 5 eq.) at 0° C. for 3 min., allowed to warm to room temperature and stirred for 100 min. The reaction was cooled to 0° C., neutralized by addition of HCl (1.62 mL, 2.0M in Et2O, ~pH 5.5), diluted with ethyl acetate (50 mL) washed with and separated. The aqueous layer was washed with saturated aqueous NaHCO₃ sol'n (5 mL) and separated. The aqueous layer was extracted with ethyl acetate (2×10 mL). The combined organic layer was washed with brine, dried over Na₂SO₄, filtered and evaporated to dryness. The residue was purified by silica gel column chromatography with 0~9% methanol in dichloromethane to give the compound (3-5) (0.562 g) as a white foam.

MS: (ESI) m/z (M+H) 1052.81, (M+Na) 1074.86.

Step 3e

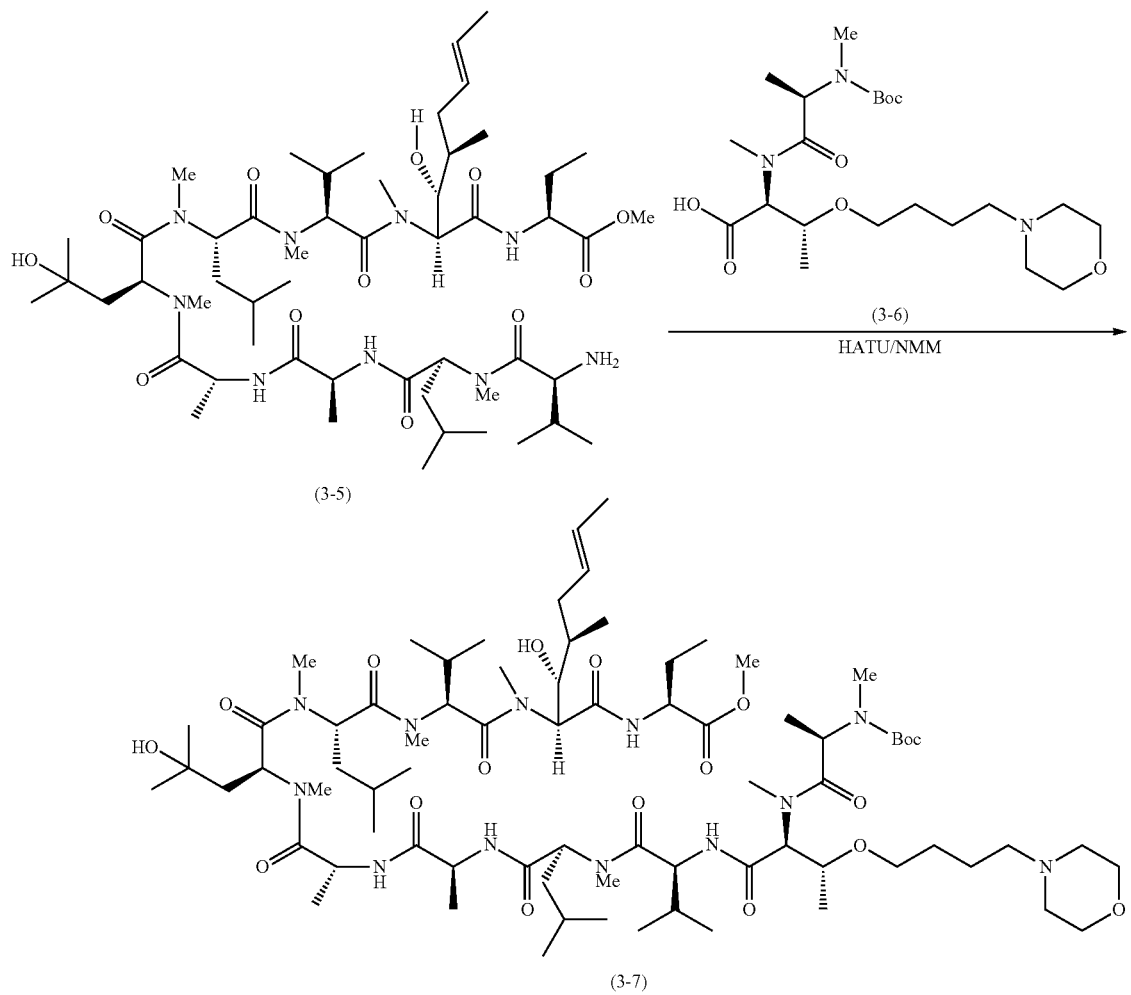

To a mixture of the compound (3-5) (0.562 g, 0.534 mmol), the compound (3-6) (0.294 g, 1.2 eq.) and 4-methylmorpholine (0.176 mL, 3.0 eq.) in dry dichloromethane (5.3 mL) was added HATU (0.284 g, 1.4 eq.) at 0° C. and stirred between 0 and 10° C. for 3 hrs. The reaction was diluted with ethyl acetate (50 mL), washed with saturated aqueous NaHCO₃ sol'n (10 mL) and separated. The aqueous layer was extracted with ethyl acetate (2×10 mL). The combined organic layer was washed with saturated aqueous NaHCO₃ sol'n (10 mL), H₂O and brine, successively. The organic layer was dried over Na₂SO₄, filtered and evaporated to dryness. The residue was purified by silica gel column chromatography with 0~50% acetone in hexanes to give the compound (3-7) (0.813 g) as a white foam.

MS: (ESI) m/z (M+H) 1494.38, (M+Na) 1516.45.

Step 3f diluted with ethyl acetate (100 mL), washed with saturated aqueous NaHCO₃ sol'n (10 mL) and separated. The aqueous layer was extracted with ethyl acetate (2×20 mL). The combined organic layer was washed with brine, dried over Na₂SO₄, filtered and evaporated to give the acid compound (0.778 g) as a white foam.

MS: (ESI) m/z (M+H) 1480.29, (M+Na) 1502.33.

To a mixture of above acid compound (0.778 g, 0.5257 mmol) in dry dichloromethane (6.6 mL) was dropwise added trifluoroacetic acid (3.3 mL, 81.5 eq.) at 0° C. for 2 min. and stirred at 0° C. for 100 min. The reaction was diluted with dichloromethane (30 mL), poured into cold saturated aqueous NaHCO₃ sol'n-20% aqueous K₂CO₃ sol'n (9:1, 70 mL) with vigorous stirring and separated. The aqueous layer was extracted with dichloromethane (2×30 mL). The combined

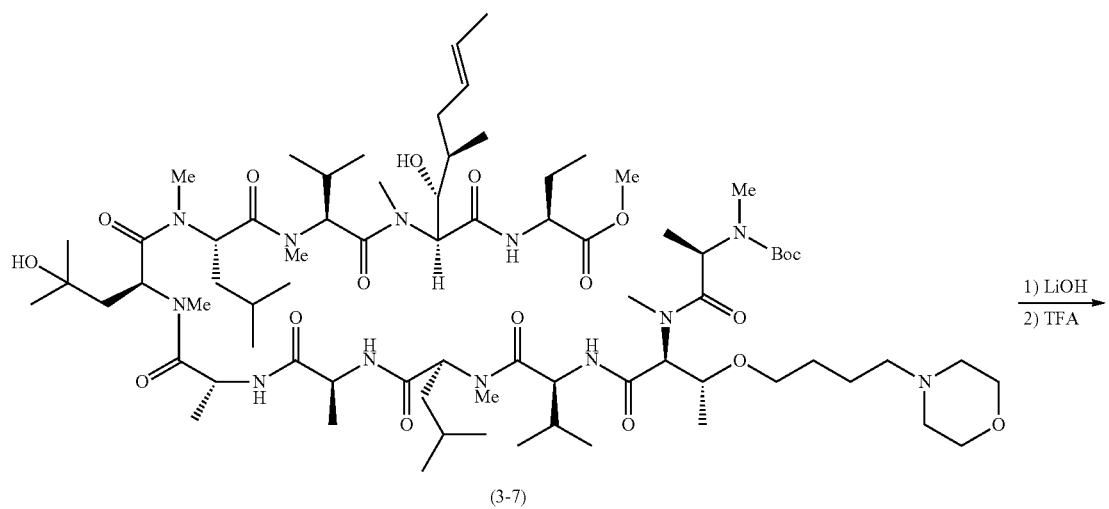

(3-7)

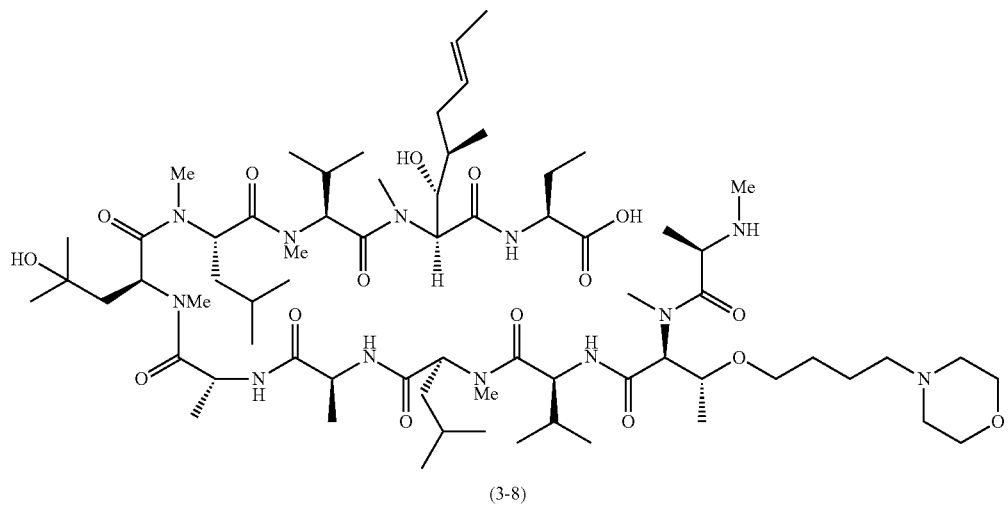

(3-8)

To a mixture of the compound (3-7) (0.797 g, 0.5334 mmol) in THF (4.8 mL) was added LiOH (2.7 mL, 0.5M in H₂O, 4.2 eq.) and at 0° C. and stirred for 3 hrs. The reaction was quenched by addition of 1M-HCl (1.5 mL, ~pH 4), organic layer was washed with brine, dried over Na₂SO₄, filtered and evaporated to give the compound (3-8) (0.614 g) a white foam.

MS: (ESI) m/z (M+H) 1380.22, (M+Na) 1402.25.

Step 3g

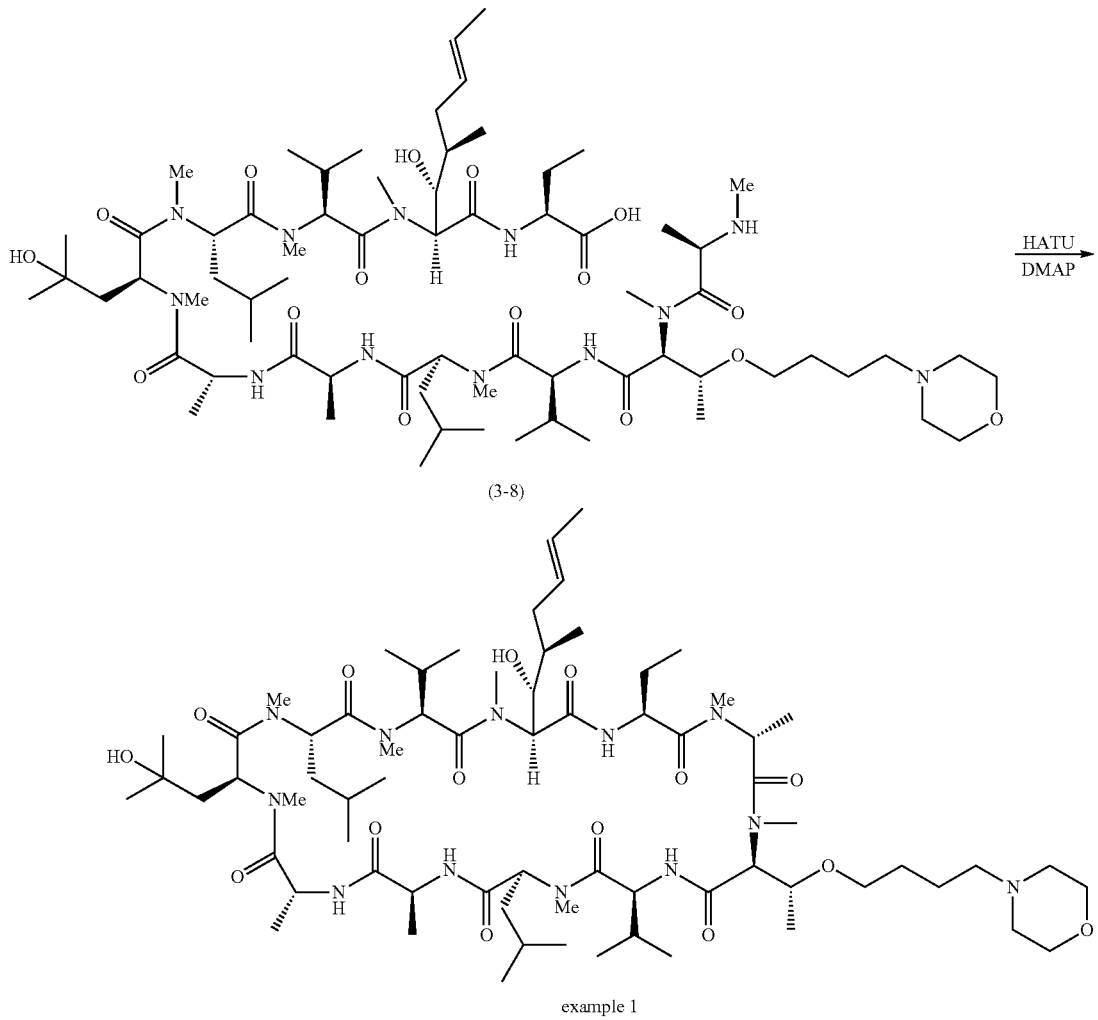

example 1

To a mixture of HATU (0.25 g, 1.5 eq.) and DMAP (0.08 g, 1.5 eq.) in dry dichloromethane (40 mL) was dropwise added the compound (3-8) (0.604 g, 0.4378 mmol) in dichloromethane (20 mL) using a dropping funnel at 30° C. for 25 min and continuously stirred at 33° C. for additional 25 min. The reaction was allowed to warm to room temperature and stirred for 15 hrs. The reaction mixture was diluted with dichloromethane (30 mL), washed with saturated aqueous NaHCO$_3$ sol'n (20 mL) and separated. The aqueous layer was extracted with dichloromethane (2×10 mL). The combined organic layer was washed with saturated aqueous NaHCO$_3$ sol'n-brine (1:1, 20 mL), dried over Na$_2$SO$_4$, filtered and evaporated to dryness. The residue was purified by silica gel column chromatography with 0~7% methanol in dichloromethane to give the crude compound of example 1 (0.405 g), which was further purified by preparative HPLC(HPLC condition: mobile phase A-20 mM NH$_4$HCO$_3$ in H$_2$O(HPLC grade); mobile phase B: Acetonitrile (HPLC grade); Luna column (pre-heated at 60° C.), flow rate: 20 mL/min; 40-95% B for 30 min.) to give the compound example 1 (0.283 g) as a white cotton after lyophilization. HPLC purity: 97.8%;

MS: (ESI) m/z (M+H) 1362.30, (M+Na) 1384.30.

Biological Activity

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. One of the HCV replicon cell lines (strain Con1, genotype 1b) has the nucleic acid sequence set forth in EMBL Accession No.: AJ242651, the coding sequence of which is from nucleotides 1801 to 8406. Another replicon cell line (strain H77, genotype 1a) was constructed as described by Yi et al. (Yi et al. (2004) Journal of Virology 78(15):7904-15). The coding sequences of the published HCV replicons were synthesized and subsequently assembled in plasmids using standard molecular biology techniques.

One replicon cell line ("SGR 11-7") stably expresses HCV replicon RNA, genotype 1b, which consists of: (i) the HCV 5'UTR fused to the first 12 amino acids of the capsid protein, (ii) the neomycin phosphotransferase gene (neo), (iii) the IRES from encephalomyocarditis virus (EMCV); and (iv) HCV NS2 to NS5B genes and the HCV 3'UTR. Another replicon cell line ("Huh-1a7") described by Yi et al. (Yi et al. (2004) Journal of Virology 78(15):7904-15, expressly incorporated by reference in its entirety) stably expresses HCV replicon RNA, genotype 1a, which consists of: (i) the HCV 5'UTR fused to the first 12 amino acids of the capsid protein, (ii) the HIV tat protein, (iii) the neomycin phosphotransferase gene (neo), (iv) the IRES from encephalomyocarditis virus (EMCV), and (vi) HCV NS3 to NS5B genes that harbor cell culture adaptive mutations (Q1067R, K1691R, S2204I) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100 X penicillin/streptomycin (Cat#15140-122, Invitrogen) and Geneticin (Cat#10131-027, Invitrogen) at 0.75 mg/ml or 0.25 mg/ml for 11-7 and Huh-1a7 cells, respectively.

2. HCV Replicon Assay—qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat# AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat# AM1812). Chemical agent cytotoxicity is evaluated using an MTS assay according to the manufacturer's directions (Promega).

The compounds of the present invention can be effective against the HCV 1a and 1b genotypes. It should also be understood that the compounds of the present invention can inhibit multiple genotypes of HCV. In one embodiment, compounds of the present invention are active against the 1a, 1b, 2a, 2b, 3a, 4a, and 5a genotypes. Table 2 shows the $EC_{50}$ values of representative compounds of the present invention against the HCV 1a and 1b genotypes from the above described qRT-PCR. $EC_{50}$ ranges against HCV 1a or 1b are as follows: A >1 µM; B 0.2~1.0 µM; C<0.2 µM.

TABLE 2

| Genotype-1a or 1b replicon $EC_{50}$ | | |
|---|---|---|
| Example | 1a $EC_{50}$ | 1b $EC_{50}$ |
| CsA | B | B |
| Allisporivir | C | C |
| 1 | C | C |

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:

1. A compound represented by the formula (I) or (II):

(I)
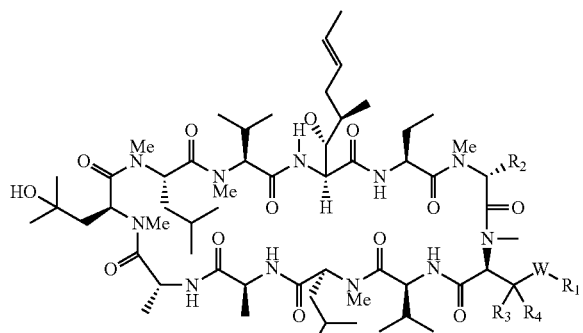

(II)
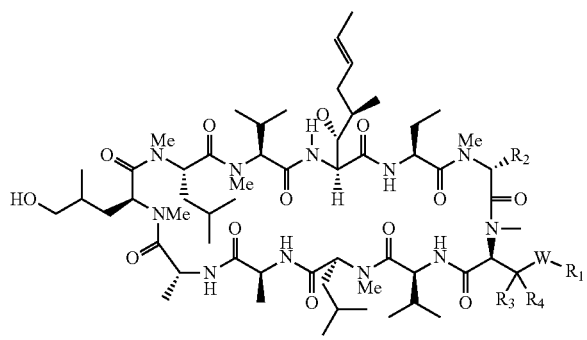

or a pharmaceutically acceptable salt, ester or prodrug thereof,
wherein $R_1$ is selected from:
a) $R_{11}$, wherein $R_{11}$ is selected from:
1) Hydrogen;
2) Deuterium;
3) $C_1$-$C_8$ alkyl;
4) Substituted $C_1$-$C_8$ alkyl;
5) $C_2$-$C_8$ alkenyl;
6) Substituted $C_2$-$C_8$ alkenyl;
7) $C_2$-$C_8$ alkynyl;
8) Substituted $C_2$-$C_8$ alkynyl;
9) $C_3$-$C_{12}$ cycloalkyl;
10) Substituted $C_3$-$C_{12}$ cycloalkyl;
11) Aryl;
12) Substituted aryl;
13) Heterocycloalkyl;
14) Substituted heterocycloalkyl;
15) Heteroaryl; and
16) Substituted heteroaryl;
b) —C(O)N($R_{12}$)($R_{13}$), wherein $R_{12}$ and $R_{13}$ are independently selected from $R_{11}$ and $R_{11}$ is as previously defined or $R_{12}$ and $R_{13}$ are taken together with the nitrogen atom to which they are attached to form a substituted or unsubstituted heterocycloalkyl;
c) $R_{14}$, wherein $R_{14}$ is selected from:
1) -M-$R_{11}$, wherein $R_{11}$ is as previously defined and M is selected from:
  i. $C_1$-$C_8$ alkylene;
  ii. Substituted $C_1$-$C_8$ alkylene;
  iii. $C_2$-$C_8$ alkenylene;
  iv. Substituted $C_2$-$C_8$ alkenylene;
  v. $C_2$-$C_8$ alkynylene;
  vi. Substituted $C_2$-$C_8$ alkynylene;
  vii. $C_3$-$C_{12}$ cycloalkylene;
  viii. Substituted $C_3$-$C_{12}$ cycloalkylene;
2) -M-$NR_{15}R_{18}$, wherein $R_{15}$ and $R_{18}$ are each independently $R_{11}$; or $R_{15}$ and $R_{18}$ are taken together with the nitrogen atom to which they are attached to form a substituted or unsubstituted heterocycloalkyl, and M is as previously defined;
3) -M-S(O)$_m$R$_{ii}$, wherein m=0, 1, or 2; M and R$_{11}$ are as previously defined;
4) -M-OR$_{11}$, wherein M and R$_{11}$ are as previously defined;
5) -M-C(O)R$_{16}$, wherein M is as previously defined and R$_{16}$ is selected from
 i. C$_1$-C$_8$ alkyl;
 ii. Substituted C$_1$-C$_8$ alkyl;
 iii. C$_2$-C$_8$ alkenyl;
 iv. Substituted C$_2$-C$_8$ alkenyl;
 v. C$_2$-C$_8$ alkynyl;
 vi. Substituted C$_2$-C$_8$ alkynyl;
 vii. C$_3$-C$_{12}$ cycloalkyl; and
 viii. Substituted C$_3$-C$_{12}$ cycloalkyl;
6) -M-OC(O)R$_{16}$, wherein M and R$_{16}$ are as previously defined;
7) -M-OC(O)OR$_{16}$, wherein M and R$_{16}$ are as previously defined;
8) -M-NR$_{17}$C(O)R$_{16}$, wherein R$_{17}$ is R$_{11}$, M and R$_{16}$ are as previously defined;
9) -MNR$_{17}$C(O)OR$_{16}$, wherein R$_{17}$, M and R$_{16}$ are as previously defined;
10) -M-C(O)NR$_{17}$R$_{11}$, wherein R$_{17}$, M and R$_{11}$ are as previously defined;
11) -M-C(O)N(R$_{17}$)—OR$_{11}$, wherein R$_{17}$, M and R$_{11}$ are as previously defined;
12) -M-OC(O)NR$_{17}$R$_{11}$, wherein R$_{17}$, M and R$_{11}$ are as previously defined;
13) -M-NR$_{17}$C(O)NR$_{16}$R$_{18}$, wherein M, R$_{16}$, R$_{17}$ and R$_{18}$ are as previously defined or R$_{16}$ and R$_{17}$ are taken together with the nitrogen atom to which they are attached to form a substituted or unsubstituted heterocycloalkyl;
14) -M-C(S)SR$_{11}$, wherein M and R$_{11}$ are as previously defined;
15) -M-OC(S)SR$_{16}$, wherein M and R$_{16}$ are as previously defined;
16) -M-NR$_{17}$C(O)SR$_{16}$, wherein M, R$_{17}$ and R$_{16}$ are as previously defined;
17) -M-SC(O)NR$_{17}$R$_{18}$, wherein M, R$_{18}$ and R$_{17}$ are as previously defined or R$_{17}$ and R$_{18}$ are taken together with the nitrogen atom to which they are attached to form a substituted or unsubstituted heterocycloalkyl;
18) -M-CH=N—OR$_{11}$, wherein M and R$_{11}$ are as previously defined;
19) -M-CH=N—NR$_{17}$R$_{18}$, wherein M, R$_{18}$ and R$_{17}$ are as previously defined or R$_{17}$ and R$_{18}$ are taken together with the nitrogen atom to which they are attached to form a substituted or unsubstituted heterocycloalkyl;

W is absent, or —O—, or —S(O)$_m$—, where m=0, or 1, or 2;

R$_2$, R$_3$ and R$_4$ are independently selected from: hydrogen or methyl.

2. A compound according to claim 1 which is represented by the formula (III) or (IV):

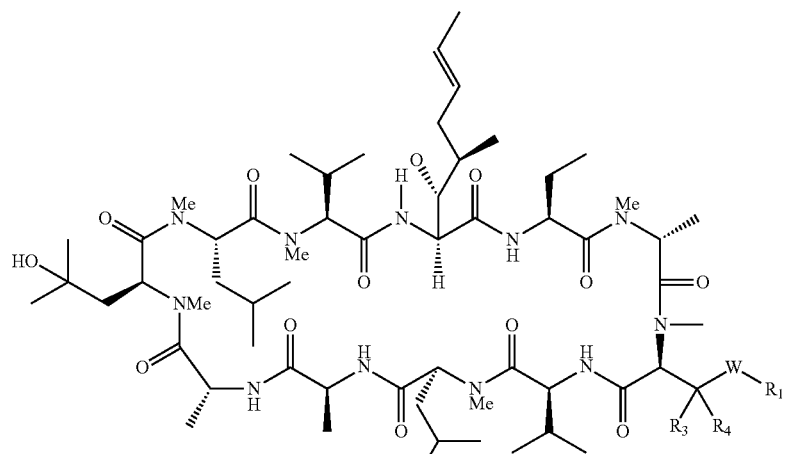

(III)

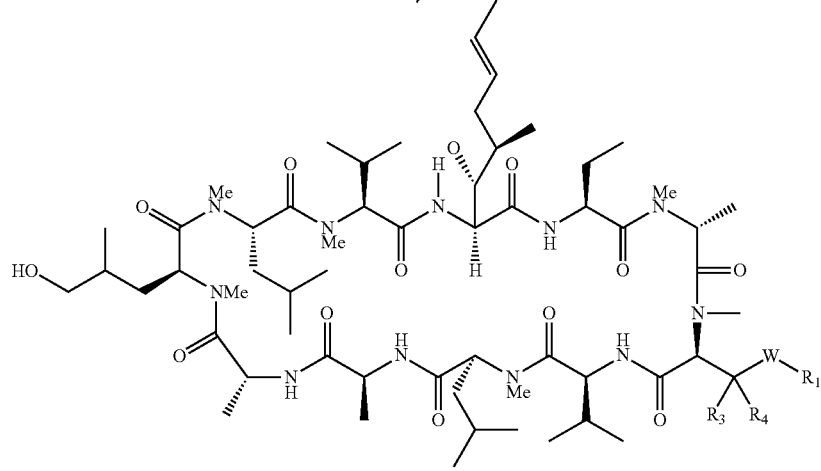

(IV)

wherein, R$_1$, R$_3$, R$_4$, W are as defined in claim 1.

3. A compound according to claim 1 which is represented by the formula (V) or (VI):
(V)
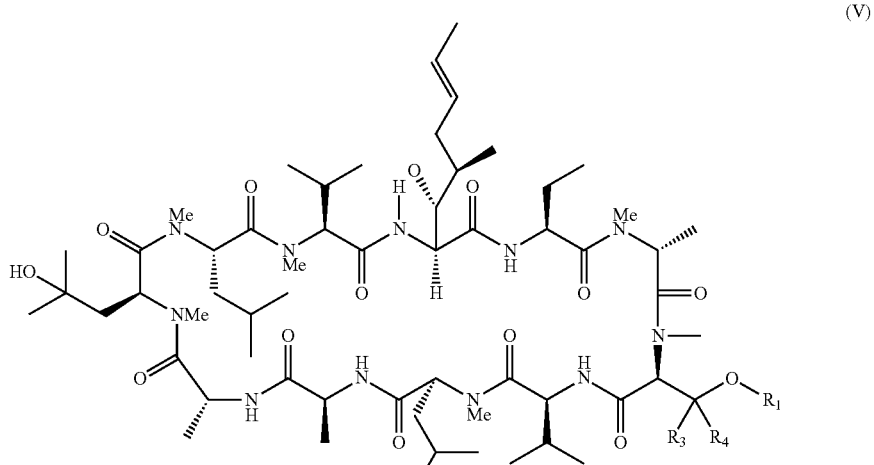
(VI)
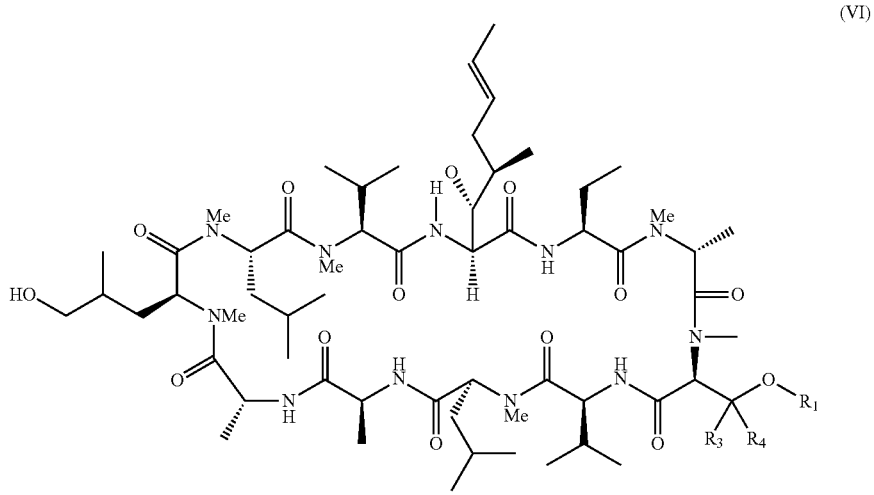
wherein, $R_1$, $R_3$, $R_4$ are as defined in claim 1.
4. A compound according to claim 1 represented by Formula VII or Formula VIII, wherein $R_1$ for each compound is set forth in Table 1:
(VII)
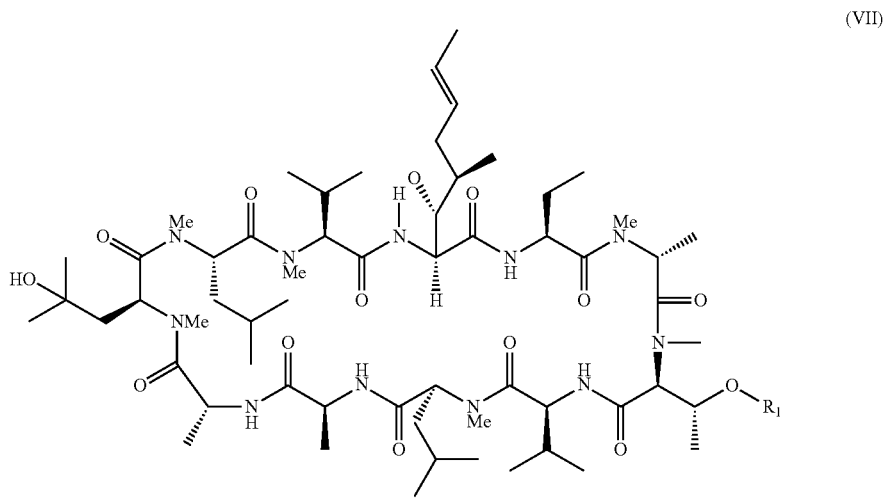

(VIII)
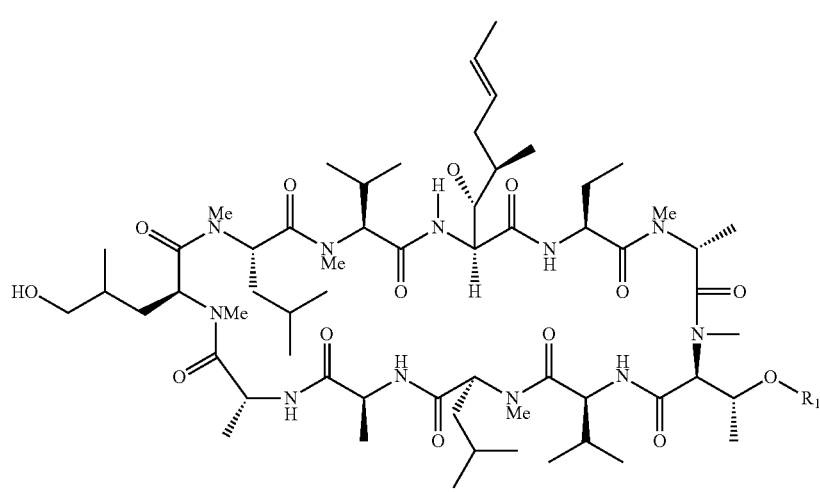
| Example | $R_1$ |
|---|---|
| 1 | -(CH2)4-morpholinyl |
| 2 | -CH2-CH=CH2 |
| 3 | -CH2-phenyl |
| 4 | -CH2-CH=CH-phenyl |
| 5 | -CH2-CH=CH-CH2-OH |
| 6 | -CH2-CH=CH-CH2-NEt2 |
| 7 | -CH2-CH=CH-CH2-morpholinyl |
| 8 | Ac |
| 9 | -(CH2)4-(4-methylpiperazinyl) |
| 10 | -(CH2)4-(1-tetrazolyl) |
| 11 | -(CH2)4-N3 |
| 12 | -(CH2)4-O-C(O)-morpholinyl |
| 13 | -(CH2)3-CH=N-OMe |
| 14 | -(CH2)3-CH=N-O-CH2-(6-(1-pyrazolyl)pyridin-3-yl) |
| 15 | -(CH2)3-CH=N-NHMe |
| 16 | -(CH2)3-CH=N-(1-piperidinyl) |
| 17 | -CH2-CH2-OH |

TABLE 1-continued

| Example | R₁ |
|---|---|
| 18 | 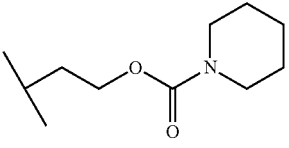 |
| 19 | 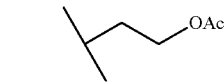 |
| 20 | 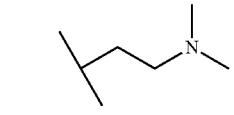 |
| 21 | 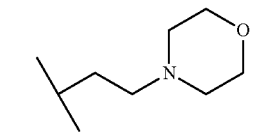 |
| 22 | 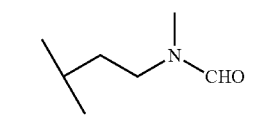 |
| 23 | 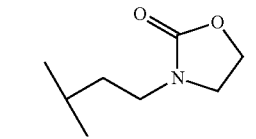 |

TABLE 1-continued

| Example | R₁ |
|---|---|
| 24 | 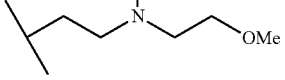 |

5. A pharmaceutical composition comprising a therapeutically effective amount of a compound of claim 1 or a pharmaceutically acceptable salt, ester or prodrug thereof, in combination with a pharmaceutically acceptable carrier.

6. A method of treating a viral infection in a subject in need thereof, comprising administering to said subject a therapeutically effective amount of the pharmaceutical composition according to claim 5.

7. The method according to claim 6, wherein said viral infection is selected from HCV, HBV, HAV and HIV infection.

8. The method of claim 6, further comprising co-administering one or more additional anti-viral agents.

9. The method of claim 6, wherein said one or more additional anti-viral agents are selected from peg-interferon, ribavirin, viral-enzyme targeted compounds, viral-genome-targeted therapies, immunomodulatory agents, Toll-receptor agonists and combinations thereof.

10. The method of claim 9, wherein said one or more additional anti-viral agents are selected from peg-interferon, viral-enzyme targeted compounds, viral-genome-targeted therapy, immunomodulatory agents, toll-receptor agonists and combinations thereof.

11. The method of claim 10, wherein said viral-genome-targeted therapy is selected from RNA interference.

12. The method of claim 10, wherein said immunomodulatory agent is selected from ribavarin and interferon.

* * * * *